(12) United States Patent
Roberts et al.

(10) Patent No.: US 11,583,622 B2
(45) Date of Patent: Feb. 21, 2023

(54) SUCTION CANISTER AND CORRESPONDING SYSTEMS AND METHODS

(71) Applicant: Medline Industries, LP, Northfield, IL (US)

(72) Inventors: Derek Roberts, Chicago, IL (US); Brian Barkeley, Chicago, IL (US); Zach Zott, Chicago, IL (US); Stuart Mintz, Glenview, IL (US); Thomas D. Mills, Highland Park, IL (US)

(73) Assignee: Medline Industries, LP, Northfield, IL (US)

( * ) Notice: Subject to any disclaimer, the term of this patent is extended or adjusted under 35 U.S.C. 154(b) by 593 days.

(21) Appl. No.: 16/788,180

(22) Filed: Feb. 11, 2020

(65) Prior Publication Data

US 2020/0188562 A1 Jun. 18, 2020

Related U.S. Application Data

(60) Division of application No. 15/214,280, filed on Jul. 19, 2016, now Pat. No. 10,596,305, which is a (Continued)

(51) Int. Cl.
*A61M 1/00* (2006.01)

(52) U.S. Cl.
CPC .............. *A61M 1/78* (2021.05); *A61M 1/604* (2021.05); *A61M 1/743* (2021.05); (Continued)

(58) Field of Classification Search
CPC ........ A61M 1/604; A61M 1/743; A61M 1/78; A61M 2205/583; A61M 2205/584; A61M 2209/084
See application file for complete search history.

(56) References Cited

U.S. PATENT DOCUMENTS 3,814,098 A 6/1974 Deaton
3,866,608 A 2/1975 Reynolds et al.
(Continued)

FOREIGN PATENT DOCUMENTS

AU 649128 5/1994
CN 201353366 12/2009
(Continued)

OTHER PUBLICATIONS

Medi-Vac Suction and Fluid Collection Products Catalog; CRD Hardware; Cardinal Health; Copyright 20013; Unknown Publication date but prior to filing of present application.
(Continued)

*Primary Examiner* — Kai H Weng
(74) *Attorney, Agent, or Firm* — Philip H. Burrus, IV

(57) ABSTRACT

A canister lid (101) for a canister (102) includes an annular perimeter (103) surrounding an interior portion (104). Rather than completely surrounding the interior portion, the annular perimeter is instead interrupted by a suction conduit (112) defined by a suction conduit (112) separating a first lobe (117) and a second lobe (118). The suction conduit (112) intersects the annular perimeter such that the first lobe is disposed interior of the annular perimeter while the second lobe is disposed exterior to the annular perimeter. The canister lid can further include one or more ports (110,111) extending from the interior portion. A canister (102) can include a valve (401) and can optionally be coupled to a hub mount vacuum source (1200) or a hub mount stand (1800).

19 Claims, 20 Drawing Sheets

Related U.S. Application Data continuation-in-part of application No. 15/005,741, filed on Jan. 25, 2016, now Pat. No. 10,398,807.

(52) U.S. Cl.
CPC . *A61M 2205/583* (2013.01); *A61M 2205/584* (2013.01); *A61M 2209/084* (2013.01)

(56) References Cited

U.S. PATENT DOCUMENTS

| | | |
|---|---|---|
| 4,321,922 A | 3/1982 | Deadon |
| 4,379,455 A | 4/1983 | Deaton |
| 4,419,093 A | 12/1983 | Deaton |
| 4,430,084 A | 2/1984 | Deaton |
| 4,460,361 A | 7/1984 | Nichols |
| 4,681,571 A | 7/1987 | Nehring |
| 4,802,506 A | 2/1989 | Aslanian |
| 5,185,007 A | 2/1993 | Middaugh et al. |
| 5,234,419 A | 8/1993 | Bryant et al. |
| 5,279,602 A | 1/1994 | Middaugh et al. |
| 5,470,324 A | 11/1995 | Cook et al. |
| 5,624,417 A | 4/1997 | Cook et al. |
| 5,725,516 A | 3/1998 | Cook et al. |
| 5,792,126 A | 8/1998 | Tribastone et al. |
| 5,944,703 A | 8/1999 | Dixon et al. |
| 6,053,896 A | 4/2000 | Wilson et al. |
| 6,056,731 A | 5/2000 | Koetke et al. |
| 6,071,095 A | 6/2000 | Verkaat |
| 6,093,230 A | 7/2000 | Johnson, III et al. |
| 6,342,048 B1 | 1/2002 | Verkaart et al. |
| 6,575,946 B2 | 6/2003 | Sealfon |
| 6,626,877 B2 | 9/2003 | Anderson et al. |
| 6,652,495 B1 | 11/2003 | Walker |
| 6,663,586 B2 | 12/2003 | Verkaart et al. |
| 6,672,477 B2 | 1/2004 | Miller et al. |
| 6,673,055 B2 | 1/2004 | Bemis et al. |
| 6,780,309 B2 | 8/2004 | Haldopoulos et al. |
| 7,115,115 B2 | 10/2006 | Bemis et al. |
| 7,153,294 B1 | 12/2006 | Farrow |
| 7,481,243 B2 | 1/2009 | Michaels et al. |
| 7,585,292 B2 | 9/2009 | Anderson et al. |
| 7,674,248 B2 | 3/2010 | Anderson et al. |
| 7,806,879 B2 | 10/2010 | Brooks et al. |
| 8,118,796 B2 | 2/2012 | Rajamaki |
| 8,715,255 B2 | 5/2014 | Christen |
| 2005/0139532 A1 | 6/2005 | Hershberger et al. |
| 2007/0016152 A1 | 1/2007 | Karpowicz |
| 2008/0004574 A1 | 1/2008 | Dyar et al. |
| 2009/0030384 A1 | 1/2009 | Christen et al. |
| 2009/0247968 A1 | 10/2009 | Brooks |
| 2010/0241091 A1 | 9/2010 | Wu |
| 2013/0197471 A1* | 8/2013 | Williams ............ A61M 3/0229 604/247 |
| 2014/0236129 A1 | 8/2014 | Radi et al. |
| 2015/0141943 A1 | 5/2015 | Koch et al. |

FOREIGN PATENT DOCUMENTS

| | | |
|---|---|---|
| DE | 102008027486 | 12/2009 |
| EP | 0466884 | 5/1996 |
| EP | 0659090 | 2/1999 |
| EP | 0830152 | 5/2003 |
| EP | 983098 | 10/2004 |
| EP | 831943 | 12/2004 |
| EP | 858347 | 3/2005 |
| EP | 1225930 | 11/2006 |
| FR | 2639543 | 11/1988 |
| JP | 04077517 | 4/2008 |
| WO | 92014496 | 9/1992 |
| WO | 9414045 | 6/1994 |
| WO | 96011031 | 4/1996 |
| WO | 97000090 | 1/1997 |
| WO | 9714450 | 4/1997 |
| WO | 9855164 | 12/1998 |
| WO | 01072350 | 10/2001 |
| WO | 2005025666 | 3/2005 |
| WO | 2008/144951 | 12/2008 |
| WO | 2015055893 | 4/2015 |
| WO | 01024846 | 1/2016 |

OTHER PUBLICATIONS

Medi-Vac Suction and Fluid Collection Products; Flex Advantage Suction Canister System; Publication; Cardinal Health; Unknown publication date prior to filing of present application.

Weng, Kai , "Final Office Action", U.S. Appl. No. 15/214,280, filed Jul. 19, 2016; dated Oct. 8, 2019.

Weng, Kai , "NonFinal OA", U.S. Appl. No. 15/005,741, filed Jan. 25, 2016; Mailed Feb. 21, 2018.

Weng, Kai , "NonFinal OA", U.S. Appl. No. 15/214,280, filed Jul. 19, 2016; Mailed Mar. 29, 2019.

Weng, Kai , "NonFinal OA", U.S. Appl. No. 15/437,232, filed Feb. 20, 2017; Mailed Mar. 4, 2019.

Weng, Kai , "Notice of Allowance", U.S. Appl. No. 15/005,741, filed Jan. 25, 2016; dated Jan. 23, 2019.

Weng, Kai , "Notice of Allowance", U.S. Appl. No. 15/214,280, filed Jul. 19, 2016; dated Feb. 4, 2020.

Weng, Kai H. , "Final Office Action", U.S. Appl. No. 15/005,741, filed Jan. 25, 2016; dated Aug. 24, 2018.

* cited by examiner

SUCTION CANISTER AND CORRESPONDING SYSTEMS AND METHODS

CROSS REFERENCE TO PRIOR APPLICATIONS

This application is a divisional application claiming priority and benefit under 35 USC § 121 from U.S. application Ser. No. 15/214,280, filed Jul. 19, 2016, which is a continuation-in-part claiming priority and benefit under 35 USC § 120 from U.S. application Ser. No. 15/005,741, filed Jan. 25, 2016, each of which is incorporated by reference for all purposes.

BACKGROUND

Technical Field

This disclosure relates generally to medical devices, and more particularly to medical suction devices.

Background Art

Medical professionals, such as surgeons, use vacuum-like devices to remove excess fluids during medical procedures. For example, during a surgical procedure, a surgeon will couple a suction device to a fluid collection canister by way of a flexible tube. The suction device draws unwanted fluids from the surgical site into the canister. A coagulant can then be added to the fluid to transform it to a solid or semi-solid for disposal. Fluid collection canisters are used to collect and dispose of fluids in a variety of medical procedures.

Fluid collection canisters have evolved over the years. In the early twentieth century, fluid collection canisters were manufactured from glass. After a particular procedure, the glass canister was sterilized and reused. Sometime around the 1960's, plastic fluid collection canisters, such as those manufactured from polystyrene, began to replace glass canisters. The polystyrene canisters were disposable, thereby reducing the chance of a patient getting an infection or other malady as a result of improper sterilization.

In the 1990's, to combat the large amount of waste associated with discarding entire fluid collection canisters, liners were introduced. Rather than capturing fluid in the canister itself, fluids were captured in a disposable lining. The introduction of liners reduced both cost and the amount of waste.

Regardless of the type of canister used, little has changed in how the canister operates. With traditional suction canister systems, hoses are connected to ports disposed along the top of the lid. Tubes can be coupled to these ports in a fluid collection application. These various tubings connected to the ports of the lid can become tangled and can be ensnared by other objects. It would be advantageously to have an improved canister system.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present disclosure.

Figure 1:
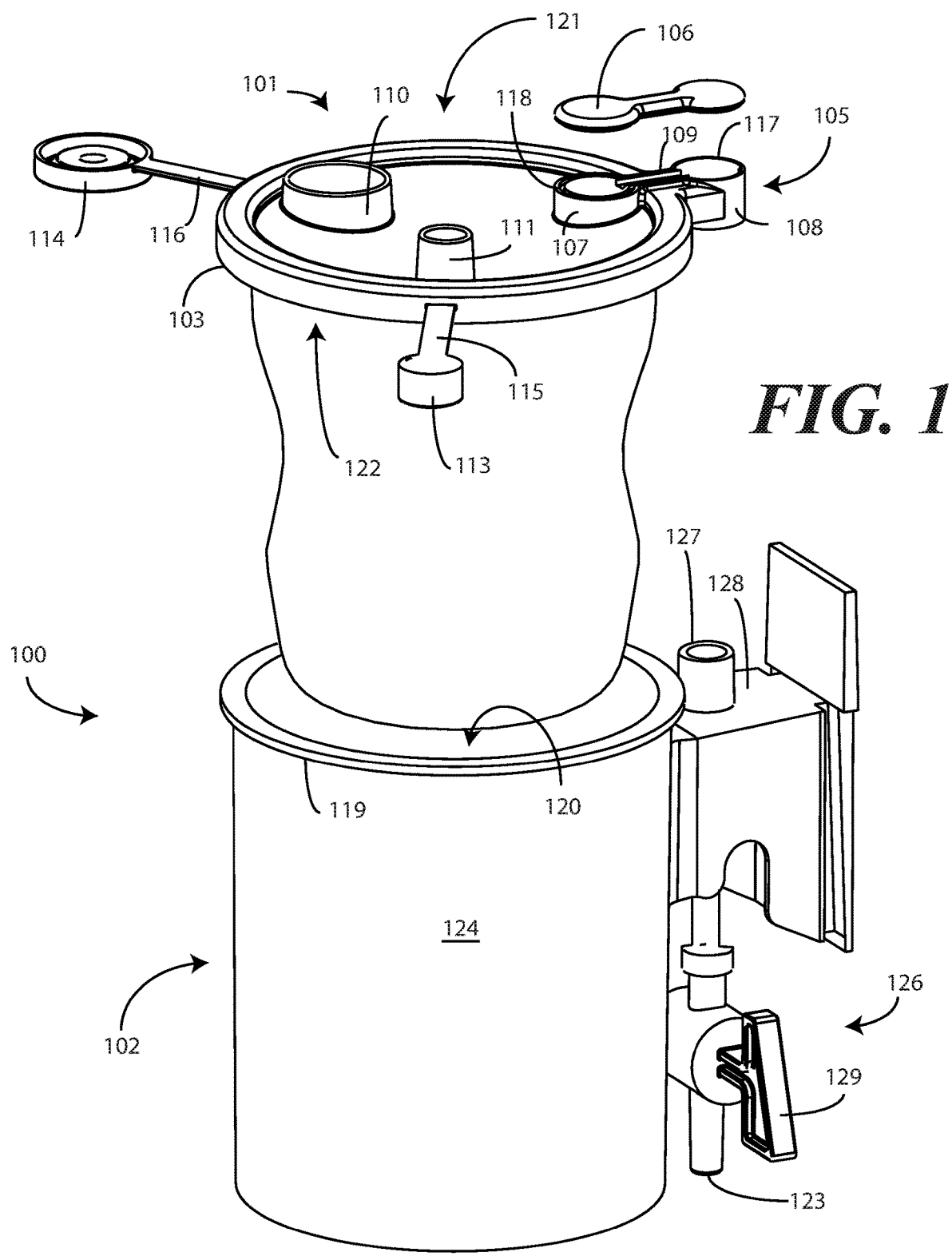
FIG. 1 illustrates an exploded view of one explanatory canister system in accordance with one or more embodiments of the disclosure

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on."

Relational terms such as first and second, top and bottom, and the like may be used solely to distinguish one entity or action from another entity or action without necessarily requiring or implying any actual such relationship or order between such entities or actions. The terms "substantially" and "about" are used to refer to dimensions, orientations, or alignments inclusive of manufacturing tolerances. Thus, a "substantially orthogonal" angle with a manufacturing tolerance of plus or minus two degrees would include all angles between 88 and 92, inclusive.

Reference designators shown herein in parenthesis indicate components shown in a figure other than the one in discussion. For example, talking about a device (10) while discussing figure A would refer to an element, 10, shown in figure other than figure A. The apparatus components shown below have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

Embodiments of the disclosure provide suction canisters, suction canister lids, switches suitable for use with suction canisters, and suction canister stands and mounts suitable for use in medical fluid collection operations. Advantageously, in one or more embodiments the canisters and canister lids eliminate one or more of the tubes or hoses required with prior art systems. Not only does this reduce system complexity and cost, it makes setup and breakdown of canister systems configured in accordance with embodiments of the disclosure faster and more efficient as well.

In one or more embodiments, a canister is coupled to a canister lid that includes an annular perimeter surrounding an interior portion. Instead of including a suction port and an exhaust port along the interior of the lid, in one embodiment the canister lid includes a suction conduit extending from a perimeter of the canister lid. In one embodiment, the suction conduit interrupts the annular perimeter with a portion of the suction duct that extends distally away from the annular perimeter.

In one or more embodiments, the suction conduit includes a suction duct that separates a first lobe and a second lobe. In one or more embodiments, the first lobe and the second lobe are substantially circular, while the suction duct is substantially straight. Accordingly, in such an embodiment when the suction conduit is viewed in plan view, the suction conduit can resemble a dog bone or double-ended lollipop.

In one or more embodiments, the suction duct separates the first lobe and the second lobe and traverses or intersects the annular perimeter such that the first lobe is disposed interior of the annular perimeter while the second lobe is disposed exterior to the annular perimeter. In one embodiment, the second lobe is operable to engage a suction port extending distally from the sidewall of a canister when the annular perimeter engages the lip of the canister. Advantageously, air can flow from the second lobe through the suction duct to the first lobe, or vice versa, such that the suction conduit serves as either a suction input or an exhaust. This eliminates the need for at least one tube or hose in fluid collection operations.

The canister lid can be coupled to a canister that is equipped to receive suction from a vacuum tube or hose in one or more embodiments. Advantageously, the vacuum tube or hose is the only hose or tube required to provide complete suction to the canister due to the fact that air flows from the vacuum tube input of the canister through the second lobe, suction duct, and first lobe of the canister lid into the canister. Accordingly, while prior art systems would require additional tubes or hoses to couple ducts of a prior art lid to the vacuum tube input, one or more embodiments of the disclosure require only a single vacuum tube or hose rather than multiple ones.

In other embodiments, the canister becomes completely tubeless in that it is configured to couple directly to a stand that couples—without hoses or tubes—a vacuum source within the stand to the vacuum input of the canister. This "plug and play" vacuum system allows canisters to freely be coupled to, or decoupled from, the stand as needed. The stand can be equipped with switches or push buttons that medical personnel can actuate to turn a particular vacuum port ON or OFF, depending upon whether a corresponding canister is coupled to a receiver associated with the vacuum port. In one or more embodiments, the stands are separable so that they can be cleaned as well.

In some embodiments, the canister is configured to either be attached to a stand in a tubeless system or coupled to a vacuum port or hose directly. Accordingly, medical personnel can use canisters configured in accordance with embodiments of the disclosure with legacy hose-based systems or with stands configured in accordance with one or more embodiments of the disclosure.

In one or more embodiments, the canister can be configured with simple switches that allow medical personnel to selectively turn ON or OFF suction to an individual canister. These switches can be configured a push-button style switches, rotational switches, slider switches, or other types of switches. In one or more embodiments, the switches include easily visible indicia that indicate whether suction is turned ON or OFF. In some embodiments, the switches are selectively removable from the canister body so that they can be cleaned and/or replaced as necessary.

Turning now to FIG. 1, illustrated therein is a canister system 100 configured in accordance with one or more embodiments of the disclosure. The canister system 100 includes a canister lid 101 and a canister 102. Attached to the canister lid 101 in this embodiment is a disposable liner operable to catch fluids or other materials drawn in through the suction port.

In one or more embodiments, the canister lid 101 is manufactured as a unitary, singular, integrated part where, for example, the annular perimeter 103, interior portion 104, the ports 110,111, suction conduit 112, caps 113,114, and tabs 115,116 comprise a single part. However, in the illustrative embodiment of FIG. 1, the suction conduit 112 comprises a separate suction conduit cap 106 coupled to each of the first lobe annular wall 107, the second lobe annular wall 108, and the one or more suction duct sidewalls 109. The suction conduit cap 106 can be adhesively sealed to each of the first lobe annular wall 107, the second lobe annular wall 108, and the one or more suction duct sidewalls 109 in one embodiment. Alternatively, the suction conduit cap 106 can be thermally or ultrasonically welded to each of the first lobe annular wall 107, the second lobe annular wall 108, and the one or more suction duct sidewalls 109 in other embodiments. Other manufacturing processes for adhering the suction conduit cap 106 to each of the each of the first lobe annular wall 107, the second lobe annular wall 108, and the one or more suction duct sidewalls 109 will be obvious to those of ordinary skill in the art having the benefit of this disclosure.

In one or more embodiments, the canister lid 101 can be manufactured from a thermoplastic material by way of an injection molding process. For example, in one embodiment, the canister lid 101 is manufactured from polypropylene. In another embodiment, the canister lid 101 is manufactured from polyethylene. It will be obvious to those of ordinary skill in the art having the benefit of this disclosure that other suitable semi-rigid materials may be substituted for the thermoplastic. Further, other manufacturing processes may be used to fabricate the canister lid 101 as well.

In the illustrative embodiment of FIG. 1, the canister lid 101 includes an annular perimeter 103 surrounding an interior portion 104. In one embodiment, the annular perimeter 103 defines a substantially circular (when viewed in plan view) sidewall surrounding the interior portion 104. In one or more embodiments, the annular perimeter 103 is operable as a "canister connector" in that it is configured to connect to a canister, one example of which is a fluid collection canister.

In one embodiment, the canister lid 101 also includes a suction conduit 112. As shown in FIG. 1, in one embodiment the suction conduit 112 comprises a suction duct defined by the suction duct sidewalls 109, a first lobe 117, and a second lobe 118. In this illustrative embodiment, rather than completely surrounding the interior portion 104, the suction conduit 112 instead interrupts the annular perimeter 103. In one embodiment the suction conduit 112 separating the first lobe 117 and the second lobe 118 traverses or intersects the annular perimeter 103 such that the first lobe 117 is disposed interior of the annular perimeter 103 along the interior portion 104 of the canister lid 101, while the second lobe 118 is disposed exterior to, and extends distally away from an outer edge of, the annular perimeter 103.

In one or more embodiments, the first lobe 117 and the second lobe 118 are substantially circular, while the suction duct disposed between the first lobe 117 and the second lobe 118 is substantially straight. Accordingly, in such an embodiment when the suction conduit 112 is viewed in plan view, the suction conduit 112 can resemble a dog bone or double-ended lollipop. In colloquial terms, in one embodiment the center of the "dog bone" of the suction conduit 112 bisects the annular perimeter 103 with half of the dog bone, i.e., the second lobe 118 and a portion of the suction conduit 112, extending outwardly away from an outer side of the annular perimeter 103 while another half of the dog bone, i.e., the first lobe 117 and another portion of the suction conduit 112, are inside the annular perimeter 103 and traverse the interior portion 104 of the canister lid 101.

In one or more embodiments, the suction conduit 112 is hollow on the inside such that air or other fluid can be drawn through each of the first lobe 117, the suction conduit 112, and the second lobe 118. Illustrating by example, in one embodiment the bottom side of the canister lid 101 includes a first aperture disposed under the first lobe 117. There is also a second aperture disposed under the second lobe 118. Accordingly, the first lobe 117 and the second lobe 118 serve as chamber walls for the first aperture and the second aperture, respectively. As the suction duct disposed between the first lobe 117 and the second lobe 118 is hollow and connects these two chambers, air and other fluids can flow into the first aperture, through the first lobe, through the suction conduit 112, into the second lobe 118, and out of the second aperture, or vice versa. Thus, the inclusion of the suction conduit 112 advantageously allows for the elimination of a hose or tube that would traditionally be used to remove air from, or deliver air to, a suction canister.

In one embodiment, the first lobe 117 comprises a first lobe annular wall 107. Similarly, in one embodiment the second lobe 118 comprises a second lobe annular wall 108. The suction duct disposed therebetween can include one or more suction duct sidewalls 109 that connect the first lobe annular wall 107 and the second lobe annular wall 108. In this illustrative embodiment the first lobe annular wall 107 and the second lobe annular wall 108 are substantially circular in cross section. However, it should be noted that other shapes could be substituted for the generally circular first lobe annular wall 107 and second lobe annular wall 108. These sidewalls could alternatively be rectangular, triangular, take free form shapes, or be ovular, pentagonal, hexagonal, and so forth. Other shapes and configurations for the first lobe annular wall 107 and the second lobe annular wall 108 will be obvious to those of ordinary skill in the art having the benefit of this disclosure.

In this illustrative embodiment, the first lobe annular wall 107 is greater in circumference than is the second lobe annular wall 108. This results in the first lobe 117 being a "bigger circle" or "bigger end of the dog bone" than the second lobe 118. In other embodiments, the second lobe annular wall 108 may have a greater perimeter than the first lobe annular wall 107. In still other embodiments, the first lobe annular wall 107 and the second lobe annular wall 108 will have substantially equal perimeters.

In one or more embodiments, the annular perimeter 103 of the canister lid 101 is operable to connect to the lip edge 119 of the canister 102. When this occurs, the interior portion 104 spans and essentially seals the opening 120 of the canister 102. In one or more embodiments, the canister lid 101 also includes one or more ports 110,111 extending from the interior portion 104. The one or more ports 110,111 facilitate the transport of fluids, be they air, liquids, or other fluids, into and away from the canister. In this illustrative embodiment, the canister lid 101 includes two ports 110,111.

For reference, the canister lid 101 can be thought of as having a topside 121 and a "canister engaging side" 212. For convention, the topside 121 is the side exposed to the environment when the canister lid 101 is coupled to a canister 102. By contrast, the canister engaging side 122 engages the canister 102 and correspondingly is oriented toward the interior 120 of the canister 102 when the canister lid 101 seals the canister 102. In the illustrative embodiment of FIG. 1, each of the ports 110,111 extends distally from the interior portion 104 from the topside 121. By contrast, the first aperture disposed beneath the first lobe 117 and the second aperture disposed beneath the second lobe 118 are each disposed along the canister engaging side 122.

As noted above, in one or more embodiments the one or more ports 110,111 facilitate fluid collection and transport to and from a canister 102 to which the canister lid 101 is coupled. While the ports 110,111 can be arranged in any number of ways, and can accommodate any number of functions, in one embodiment a first port 111 comprises a suction port while a second port 110 comprises a pour spout.

In one or more embodiments, a tube or hose can be coupled to the suction port. A vacuum or other suction appliance is then coupled vacuum tube input 123 disposed beneath the second lobe 118. The tube or hose coupled to the suction port can then coupled to a hand-held suction device. When the vacuum or suction appliance is actuated, the vacuum draws air from the canister 102 from the vacuum tube input 123, through the first aperture disposed beneath the first lobe 117, through the suction duct, through the second lobe 118, and out the second aperture. This causes fluid to be drawn through the hand-held suction device into the suction port and into the canister 102 to which the canister lid 101 is coupled. Fluid can be prevented from entering the vacuum or suction device by way of a filter (not shown) placed beneath the first aperture disposed beneath the first lobe 117.

In other embodiments, the suction port can alternatively be used as a tandem port. A tandem port is a port that can be used to daisy chain fluid collection canisters together. For example, in some medical procedures, it will be anticipated that more fluid will be collected than can be stored in a single fluid collection canister. In such situations, it may be necessary to couple multiple fluid collection canisters together with a tandem port, such that when one gets full, fluid can be delivered to other, empty fluid collection canisters.

The pour spout can be used for a variety of purposes. Illustrating by example, in one or more embodiments the pour spout can be used for pouring solidifier into a filled canister after drawing fluids into the canister. The solidifier agglutinates the fluid, thereby making it easy to transport or dispose. In alternate embodiments, the pour spout can be used to pour fluids out of the canister.

In one or more embodiments, such as for optimal "draw" when in operation, ports not in use can be sealed with one or more caps 113,114 that are integrally tethered, in this illustrative embodiment, to the canister lid 101 by a corresponding tab 115,116. Illustrating by example, if fluids were being drawn into the suction port, cap 114 could be placed atop the pour spout to seal it. Conversely, if liquid was being poured out the pour spout, cap 113 could be placed over the suction port. Where fluids were being transported, cap 114 could be placed over the pour spout while cap 113 was placed over the suction port. In one or more embodiments, the one or more caps 113,114 are to cover the one or more ports 110,111 on a one-to-one basis.

In one or more embodiments, to prevent the caps from being lost, each cap 113,114 is tethered directly to an exterior wall of the annular perimeter 103 by a corresponding tab 115,116 that is integrally formed with, and extends distally away from, the exterior wall of the annular perimeter 103. In this illustrative embodiment, each tab 115,116 extends substantially orthogonally away from the exterior wall of the annular perimeter 103.

While the one or more ports 110,111 can be disposed in various locations across the interior portion 104 of the canister lid 101, in one embodiment the ports 110,111 and the first lobe 117 of the suction conduit 112 are roughly evenly spaced around the interior portion 104. For example, in one embodiment the first lobe 117, the pour spout, i.e., port 110, and the suction port, i.e., port 111, are each radially separated by about 120 degrees along the interior portion 104. This results in the first lobe 117 being roughly at the "twelve o'clock" position when the suction conduit 112 is oriented at the top of the canister lid 101, while port 111 is roughly at the four o'clock position and port 110 is roughly at the eight o'clock position. Arranging the first lobe 117 and one or more ports 110,111 in this orientation offers maximum separation from each element about the interior portion 104 of the canister lid 101.

In this illustrative embodiment, the one or more ports 110,111 extend distally from the topside 121 of the interior portion 104 of the canister lid 101. In one embodiment, each of the one or more ports 110,111 extends to a common height from the interior portion 104 of the canister lid 101. However, in other embodiments, to provide a mnemonic device indicating which port 110,111 is used for which function, the one or more ports 110,111 extend to different heights from the interior portion 104 of the canister lid. For instance, in this illustrative embodiment, port 111 extends distally away from the interior portion 104 farther than does port 110. Accordingly, where port 111 is a suction port and port 110 is a pour spout, port 111 can extend farther from the interior portion 104 to facilitate the connection of a hose or tube for suction operations.

In one or more embodiments, the annular perimeter 103 defines a canister lip engaging recess open to the canister engaging side 122 of the canister lid 101. In one or more embodiments, the canister lip engaging recess comprises a first annular wall, a second annular wall, and a bridge spanning the first annular wall and the second annular wall. In this illustrative embodiment, the second annular wall comprises an exterior wall of both the canister lid 101 and the annular perimeter 103. In one or more embodiments, the bridge is oriented substantially orthogonally with both the first annular wall and the second annular wall.

In one or more embodiments, the canister lip engaging recess can include mechanical features for engaging the lip 119 of the canister 102. Examples of these mechanical features include mechanical locks, snaps, and the like. In other embodiments, the canister lip engaging recess can include threads so as to be screwed onto the lip 119 of the canister 102 to form a hermetic seal. In such an embodiment, the second annular wall can include an inclined plane disposed along an interior portion of the second annular wall that defines a thread. Alternatively, a dual thread can be used. Other attachment mechanisms suitable for use in the canister lip engaging recess will be obvious to those of ordinary skill in the art having the benefit of this disclosure.

In the illustrative embodiment of FIG. 1, each of the one or more of ports 110,111 extends distally from the interior portion 104 by a height that exceeds a height of the annular perimeter 103. Said differently, in one or more embodiments a height of the first annular wall to the topside 121 from the interior portion 104 is less than a height of either of the one or more ports 110,111.

Canisters suitable for use with embodiments of the disclosure can be manufactured in different sizes. For example, in one embodiment the canister 102 is a 2400 cc canister. In another embodiment, the canister 102 is a 1500 cc canister. These sizes are exemplary only, and embodiments of the invention are not intended to be limited in this regard, as any of canisters suitable for use with the invention can be created in a wide variety of sizes.

In one embodiment, the canister 102 is manufactured from a clear, substantially rigid thermoplastic by way of an injection molding process. For example, in one embodiment the canister 102 is manufactured from clear polystyrene, which is also known sometimes by the name "crystal styrene."

In one embodiment, the canister includes a rim, which may include the lip 119 or other mating feature that is suitable for coupling to or otherwise engaging a canister lip engaging recess of a canister lid 101. In this illustrative embodiment, the canister includes a cylindrical sidewall 124 that extends from a base 125. In this illustrative embodiment, the cylindrical sidewall 124 is substantially orthogonal relative to the base 125. However, in other embodiments, the cylindrical sidewall 124 is modestly tapered outward from the base 125, such as by two degrees. In still other embodiments, the canister 102 can include tapered sidewalls that extend distally from the base 125 to the lip 119 with an outward flare. Tapered sidewalls help facilitate release of the canister 102 both from stacked configurations with other canisters and from a mold, where the canister 102 can be manufactured by injection molding. In one or more embodiments, the lip 119 extends outwardly from the cylindrical sidewall 124.

In this illustrative embodiment, the canister 102 also includes an exterior suction assembly 126. In one embodiment, the exterior suction assembly 126 includes a suction port 127 extending distally from the cylindrical sidewall 124 on a mechanical support 128 that allows the suction port 127 to attach to a central vacuum or suction apparatus in a hospital or other medical facility. Advantageously, the "overhanging dog bone" of the second lobe 118 extending from the annular perimeter 103 of a canister lid 101 configured in accordance with one or more embodiments of the disclosure allows this suction port 127 to draw air through the suction conduit 112 from the interior of the canister 102. To provide this functionality, the second lobe 118 is to engage the suction port 127 when the canister lip engaging recess of the annular perimeter 103 of a canister lid 101 engages the lip 119 of the canister 102. This will be shown in more detail in FIG. 3 below.

Figure 2:
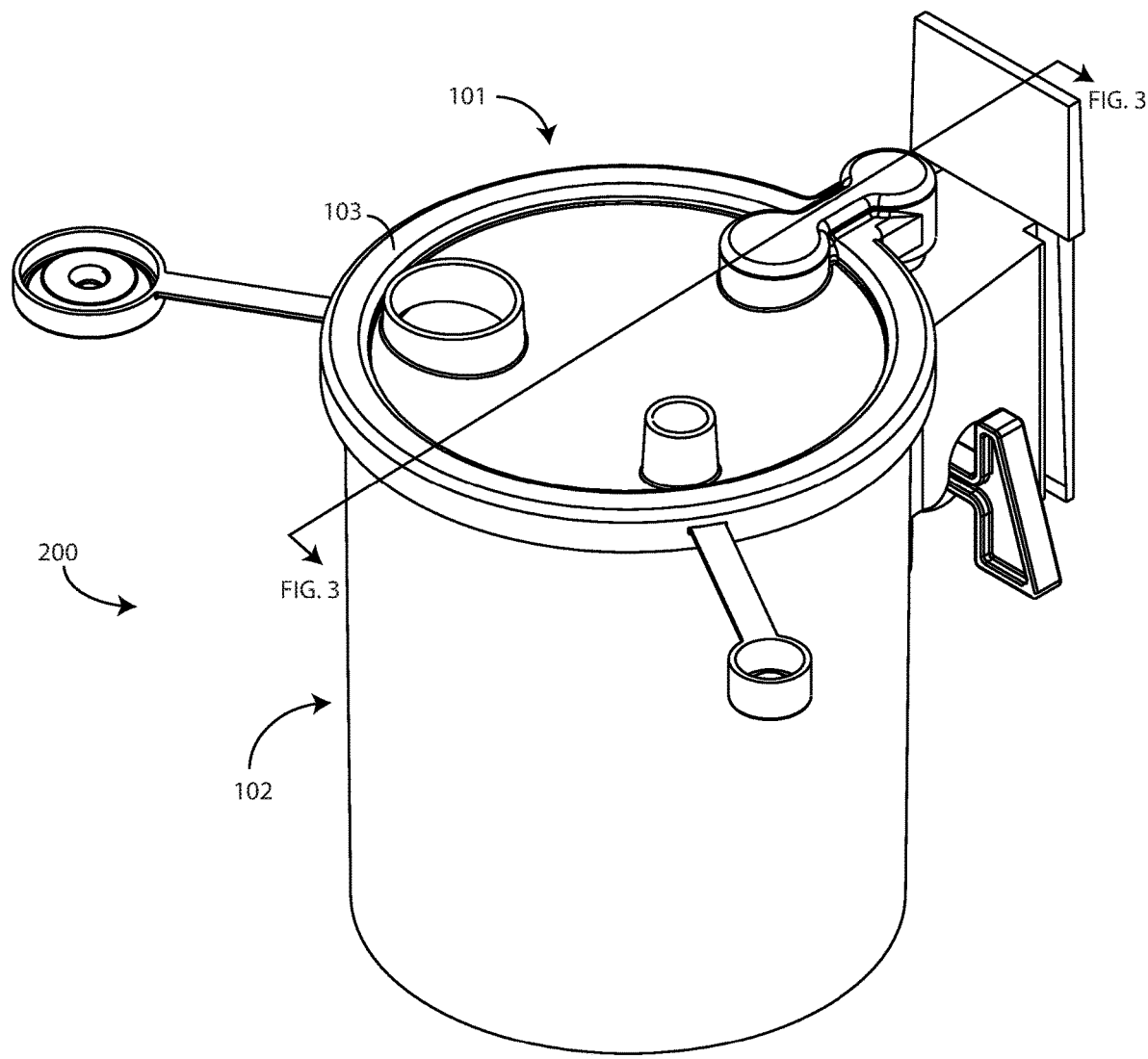
FIG. 2 illustrates a perspective view of one explanatory canister system in accordance with one or more embodiments of the disclosure.

Turning now to FIG. 2, illustrated therein is the assembled canister system 200 once the canister lid 101 has been attached to the lip (119) of the canister 102. In one or more embodiments, the second annular wall of the annular perimeter 103 can include one or more compliant coupling members to attach to the lip (119) of the canister 102. The second annular wall of the annular perimeter 103 can also be configured as cantilevered member operable to "clamp" the second annular wall of the canister lid 101 to the lip (119) of the canister 102. As shown in FIG. 2, the second lobe engages the suction port (127) of the canister 102 when the annular perimeter 103 of the canister lid 101 engages the lip (119) of the canister 102. This is shown in more detail in the sectional view of FIG. 3.

Figure 3:
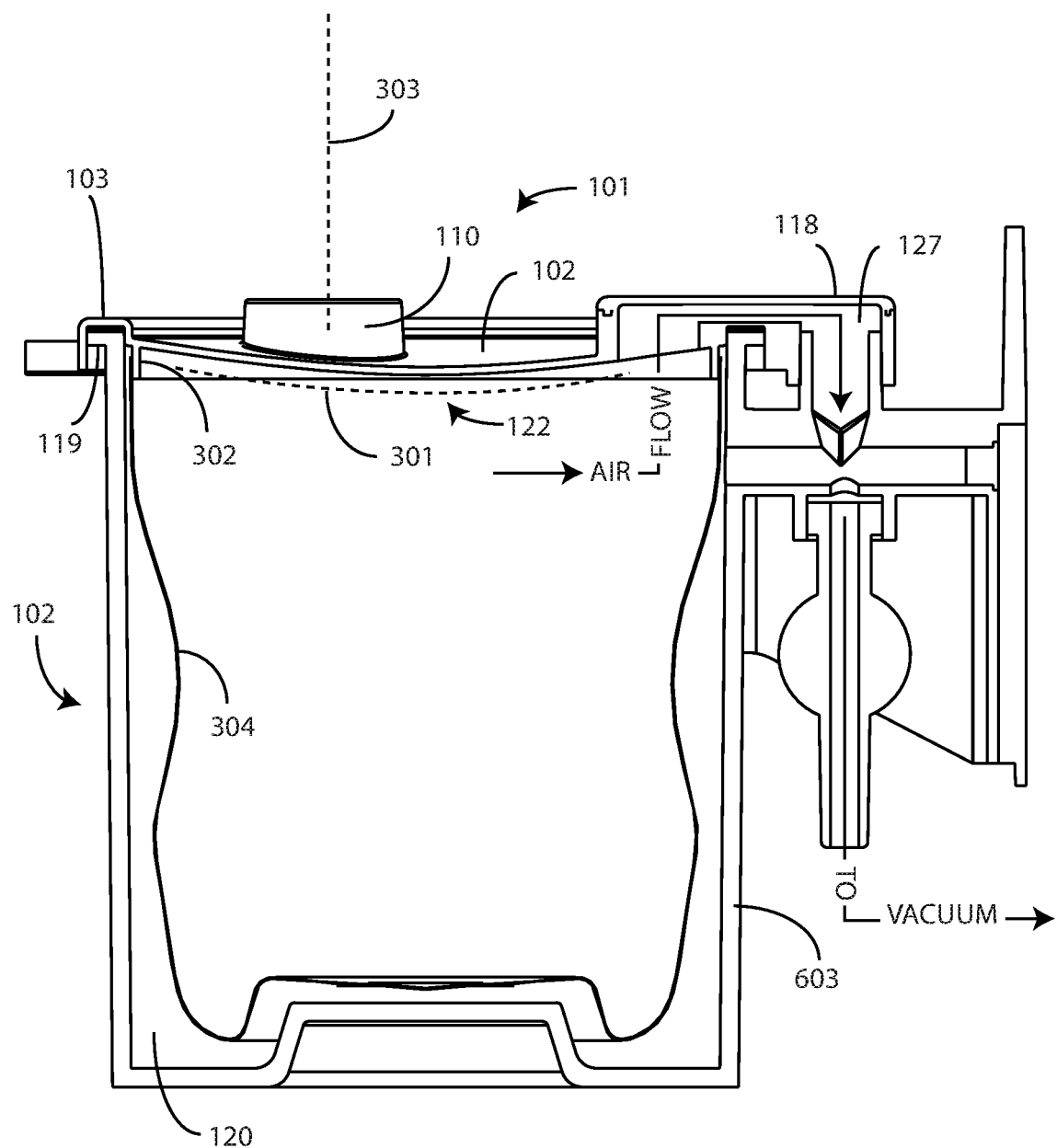
FIG. 3 illustrates a sectional view of one explanatory canister system in accordance with one or more embodiments of the disclosure.

Turning now to FIG. 3, the second lobe 118 of the canister lid 101 is shown engaging the suction port 127 of the canister 102 when the annular perimeter 103 of the canister lid 101 engages the lip 119 of the canister 102. Other features of the canister lid 101 are visible from this sectional view as well. For example, in this illustrative embodiment the interior portion 120 of the canister lid 101 defines a convex surface 301 toward the container engaging side 122 of the canister lid 101. Additionally, the interior portion 120 is shown spanning an interior of the annular perimeter 103. This convex surface 301 can be advantageous when the pressure within the canister 102 is less than outside the canister 102.

Specifically, when the canister lid 101 is sealed to the canister 102, and pressure is either removed from the exterior of the canister system 300, such as when the suction port 127 is coupled to a vacuum or other suction device, or is added to the interior of the canister 102, such as by fermentation of liquids contained within the canister 102, the convex surface 301 works as a mechanical buttress to improve the seal between the canister lid 101 and canister 102. When the convex surface 301 is pushed outward, the second annular wall of the annular perimeter 103 is pushed inward against the lip 119 of the canister 102, thereby increasing the integrity of the seal therebetween.

In the illustrative embodiment of FIG. 3, the convex surface 301 is configured to extend from the first annular wall of the annular perimeter 103 towards the canister engaging side 122 of the canister lid 101. Said differently, as viewed in FIG. 3, the convex surface 301 points downward, or toward the canister engaging side 122. In one embodiment, the portions of the interior portion 104 defining the sides of the convex surface 301 extend from the first annular wall of the annular perimeter 103 at an angle between ninety-five and one hundred and five degrees. This results in a convex surface 301 shape that is between three and ten millimeters in depth.

Another feature that can be seen in the sectional view of FIG. 3 is a barrier wall 302 extending from the interior portion 104 distally toward the canister engaging side 122 of the canister lid 101. In one or more embodiments, the barrier wall 302 is to engage the disposable liner 304 to ensure that no fluids pass outside the disposable liner into the interior portion of the canister 102 disposed between the disposable liner 304 and the cylindrical sidewall 124.

The orientation of the one or more ports 110,(111) can also be seen in the sectional view of FIG. 3. In this illustrative embodiment, a major axis 303 of the one or more ports 110,(111) is oriented substantially parallel with the barrier wall 302. In other embodiments, the major axis 303 of the one or more ports 110,(111) can be oriented orthogonally with the barrier wall 302 as taught in commonly assigned U.S. patent application Ser. No. 12/769,900, filed Apr. 29, 2010, which is incorporated herein by reference. In still other embodiments, the major axis 303 of the one or more ports 110,(111) can be oriented skew with the barrier wall 302. Other configurations will be obvious to those of ordinary skill in the art having the benefit of this disclosure.

Turning briefly back to FIG. 1, in this illustrative embodiment an exterior suction assembly 126 extends downward from the mechanical support 128 and terminates at a suction port 127. The suction port 127 can attach to a central vacuum or suction apparatus in a hospital or other medical facility. In one or more embodiments, a mechanical valve switch 129 can be rotated to open, or close, the conduit defined through the exterior suction assembly 126 to permit the central vacuum or suction apparatus to draw air from the interior of the canister 102. While this mechanical valve switch 129 works well in practice, embodiments of the disclosure contemplate that improved valve switches offer advantages when used in conjunction with the canister lids configured in accordance with embodiments of the disclosure. Examples of improved valve switches are shown in FIGS. 4-7.

Figure 4:
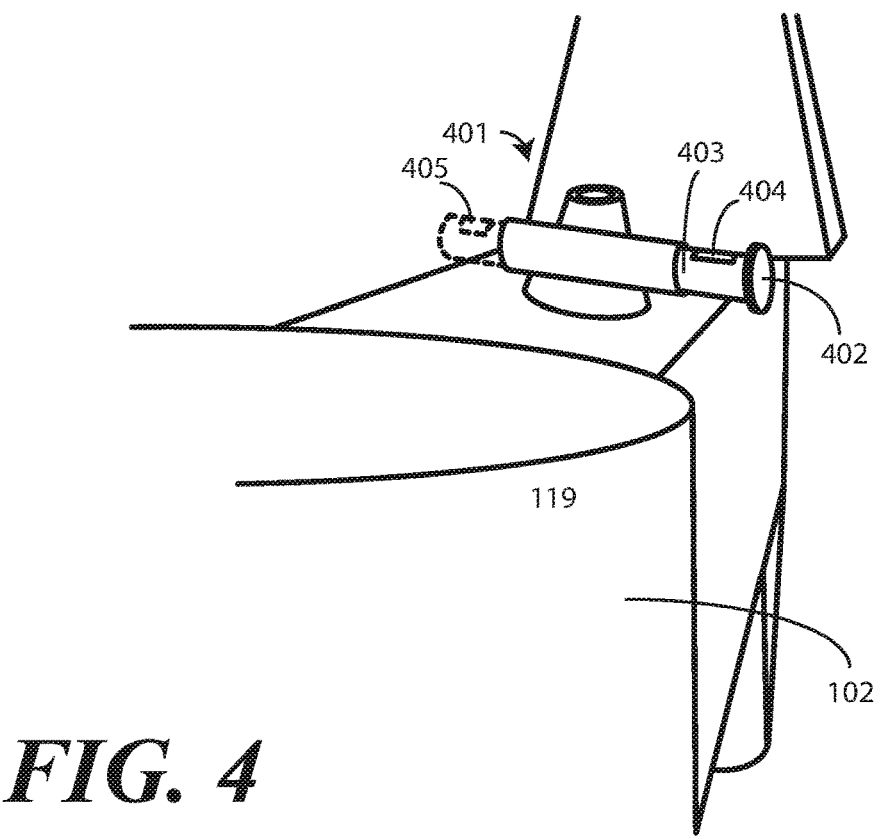
FIG. 4 illustrates one explanatory switch suitable for use in a canister system in accordance with one or more embodiments of the disclosure.

Turning now to FIG. 4, illustrated therein is one valve 401 suitable for use with a canister lid (101) configured in accordance with one or more embodiments of the disclosure. In contrast to being disposed below the mechanical support 128, as was the case in FIG. 3, in the embodiment of FIG. 4 the valve 401 is disposed atop the mechanical support 128. Accordingly, when the canister lid (101) is attached to canister 102, the valve 401 can be disposed between the second lobe (118) extending from the annular perimeter (103) when the canister lip engaging recess of the annular perimeter (103) engages the lip 119 of the canister 102.

In one embodiment, the valve 401 sits between the second lobe (118) extending from the annular perimeter (103) of a canister lid (101) and the mechanical support 128 so that a push button 402 can be accessed from beneath the canister lid (101). In this embodiment, the push button 402 is coupled to a shaft 403 that extends from the valve 401. The shaft 403 includes visual indicia 404, which in this embodiment is configured as a recess in the shaft 403. The recess can optionally be color coded to more easily indicate to a user whether the valve 401 is ON or OFF.

In one embodiment, the shaft 403 includes an aperture that aligns with the conduit defined axially in the valve 401 when the shaft 403 is in a first position. However, when the shaft 403 is translated laterally to a second position, the aperture becomes misaligned with the conduit to prevent air from flowing therethrough. Accordingly, when the shaft 403 is shown in the position of FIG. 4, with the visual indicia 404 extending from the right side of the valve 401, the valve 401 is OFF. However, by pushing the push button 402 toward the body of the valve 401, the shaft 403 translates to the left (as shown in FIG. 4) to align the aperture with the conduit. The other side of the shaft 403 would then translate out of the valve 401 to present other visual indicia 405 indicating that the valve 401 is ON. As noted, the visual indicia 404 and other visual indicia 405 may be color coded to more conveniently indicate the state of the valve 401. For example, visual indicia 404 may be red while other visual indicia 405 may be green, and so forth.

Figure 5:
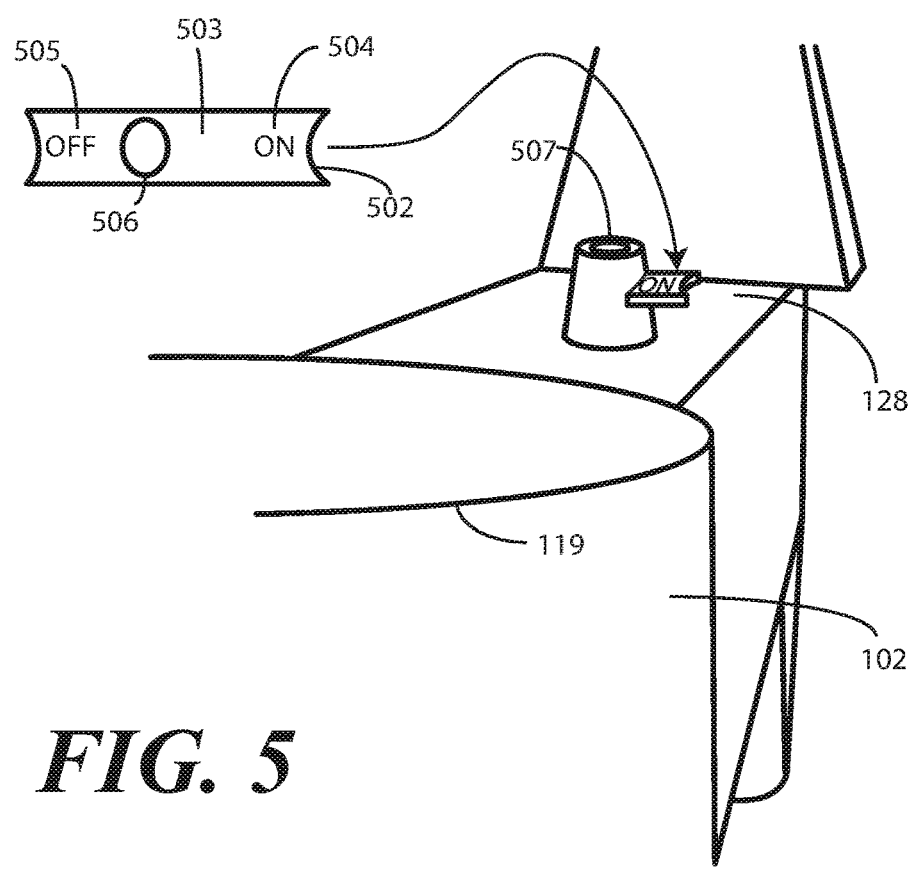
FIG. 5 illustrates another explanatory switch suitable for use in a canister system in accordance with one or more embodiments of the disclosure.

Turning now to FIG. 5, illustrated therein is a valve 501 that is similar to the valve (401) of FIG. 4, but with the shaft (403) being replaced by a plank 503. The valve 501 of FIG. 5 also differs from the valve (401) of FIG. 4 in that the push button (402) has been replaced by a concave recess 502.

As shown in FIG. 5, the valve 501 is again disposed atop the mechanical support 128. Accordingly, when the canister lid (101) is attached to the canister 102, the valve 501 is disposed between the second lobe (118) extending from the annular perimeter (103) when the canister lip engaging recess of the annular perimeter (103) engages the lip 119 of the canister 102. This allows the plank 503, and it's corresponding concave recesses 502, to be accessed from beneath the canister lid (101). As was the case with the valve (401) of FIG. 4, the plank 503 of FIG. 5 includes visual indicia 504,505, which in this embodiment is configured as the words "ON" and "OFF." Alternatively, or in combination with the words "ON" and "OFF," the visual indicia 504,505 can optionally be color coded to more easily indicate to a user whether the valve 501 is ON or OFF.

In the illustrative embodiment of FIG. 5, the plank 503 includes an aperture 506 that aligns with the conduit 507 defined axially in the valve 501 when the plank 503 is in a first position. However, when the plank 503 is translated laterally to a second position, the aperture 506 becomes misaligned with the conduit 507 to prevent the flow of air. Accordingly, when the plank 503 is shown in the position of FIG. 5, with the visual indicia 504 extending from the right side of the valve 501, the valve 501 is ON. However, by pushing the concave recess 502 toward the body of the valve 501, the plank 503 translates to the left (as shown in FIG. 5) to misalign the aperture 506 with the conduit 507. The other side of the plank 503 would then translate out of the valve 501 to present visual indicia 505 indicating that the valve 501 is OFF.

Figure 6:
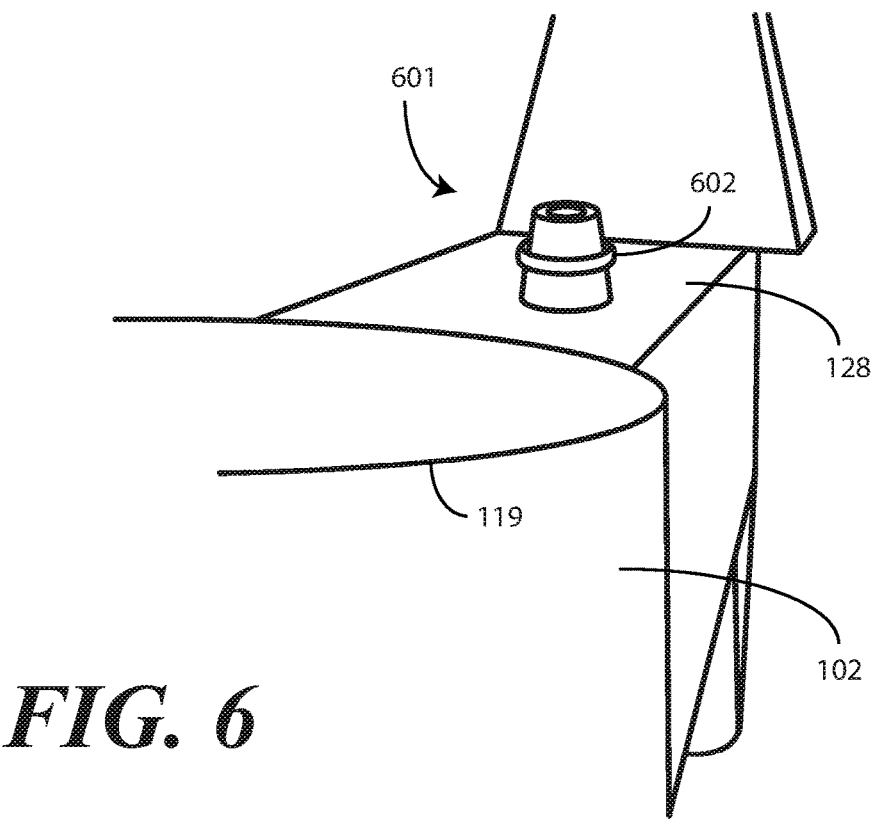
FIG. 6 illustrates yet another explanatory switch suitable for use in a canister system in accordance with one or more embodiments of the disclosure.

Turning now to FIG. 6, illustrated therein is yet another valve 601 suitable for use with one or more embodiments of the disclosure. However, rather than being a translational valve that includes a shaft (403) or plank (503) that translates into and out of a valve body, the control mechanism 602 of FIG. 6 comprises a twist component. By twisting the control mechanism 602 to one of the right or the left, the valve 601 is turned ON. By twisting the control mechanism 602 to another of the right or the left, the valve 601 is turned OFF. In one or more embodiments, the twist component is inserted into the body of the valve 601 and then covered by a glued insert.

As with the previous embodiments, the valve 601 is again disposed atop the mechanical support 128. Accordingly, when the canister lid (101) is attached to the canister 102, the valve 601 is disposed between the second lobe (118) extending from the annular perimeter (103) when the canister lip engaging recess of the annular perimeter (103) engages the lip 119 of the canister 102. This allows the control mechanism 602 to be accessed from beneath the canister lid (101). As discussed above, the control mechanism 602 can include visual indicia and/or words to easily indicate to a user whether the valve 601 is ON or OFF.

Figure 7:
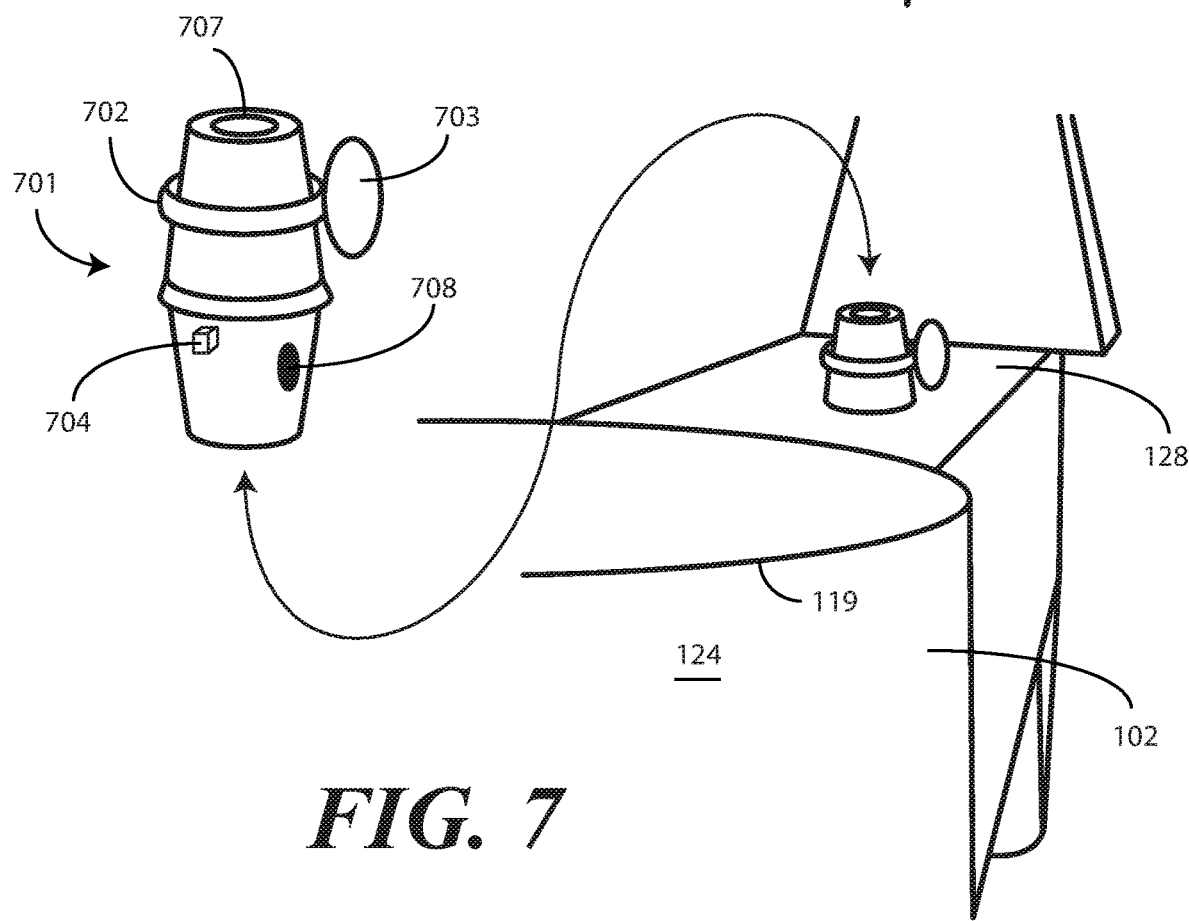
FIG. 7 illustrates still another explanatory switch suitable for use in a canister system in accordance with one or more embodiments of the disclosure.

Turning now to FIG. 7, illustrated therein is yet another valve 701 suitable for use with one or more embodiments of the disclosure. As with the valve (601) of FIG. 6, the control mechanism 702 of FIG. 7 comprises a twist component. In this illustrative embodiment, the twist component is actuated by axially rotating a paddle 703 attached to the twist component. By applying force to the paddle 703 to twist the control mechanism 702 to one of the right or the left, the valve 701 is turned ON. By applying an opposite force to the paddle 703 to twist the control mechanism 702 to the other of the right or the left, the valve 701 is turned OFF.

As with the previous embodiments, the valve 701 is again disposed atop the mechanical support 128. Accordingly, when the canister lid (101) is attached to the canister 102, the valve 701 is disposed between the second lobe (118) extending from the annular perimeter (103) when the canister lip engaging recess of the annular perimeter (103) engages the lip 119 of the canister 102. This allows the control mechanism 702 to be accessed from beneath the canister lid (101). As discussed above, the control mechanism 702 can include visual indicia and/or words to easily indicate to a user whether the valve 701 is ON or OFF.

In this illustrative embodiment, the valve 701 is removable from the canister 102 for cleaning and/or replacement. In one embodiment, the valve 701 comprises a mechanical projection 704 that sits within a corresponding mechanical recess of the mechanical support 128 to prevent the valve 701 from rotating when force is applied to the paddle 703 to twist the control mechanism 702 right or left. As with previous embodiments, the valve 701 defines a conduit 707 through which air flows when the valve 701 is ON. In one embodiment, the valve 701 further includes an air hole 708 that connects to the conduit 707 to provide suction to the cylindrical sidewall 124 to prevent the disposable liner 304 from collapsing as described above with reference to FIG. 3. It should be noted that while the valves (401,501,601) of FIGS. 4-6 were shown permanently coupled to the mechanical support 128, they could be removable as is the case with the valve 701 of FIG. 7. Additionally, while the valve 701 of FIG. 7 is shown as being removable from the mechanical support 128, it could be permanently coupled to the mechanical support as is the case with the valves (401,501, 601) of FIGS. 4-6. Other configurations will be obvious to those of ordinary skill in the art having the benefit of this disclosure.

Figure 8:
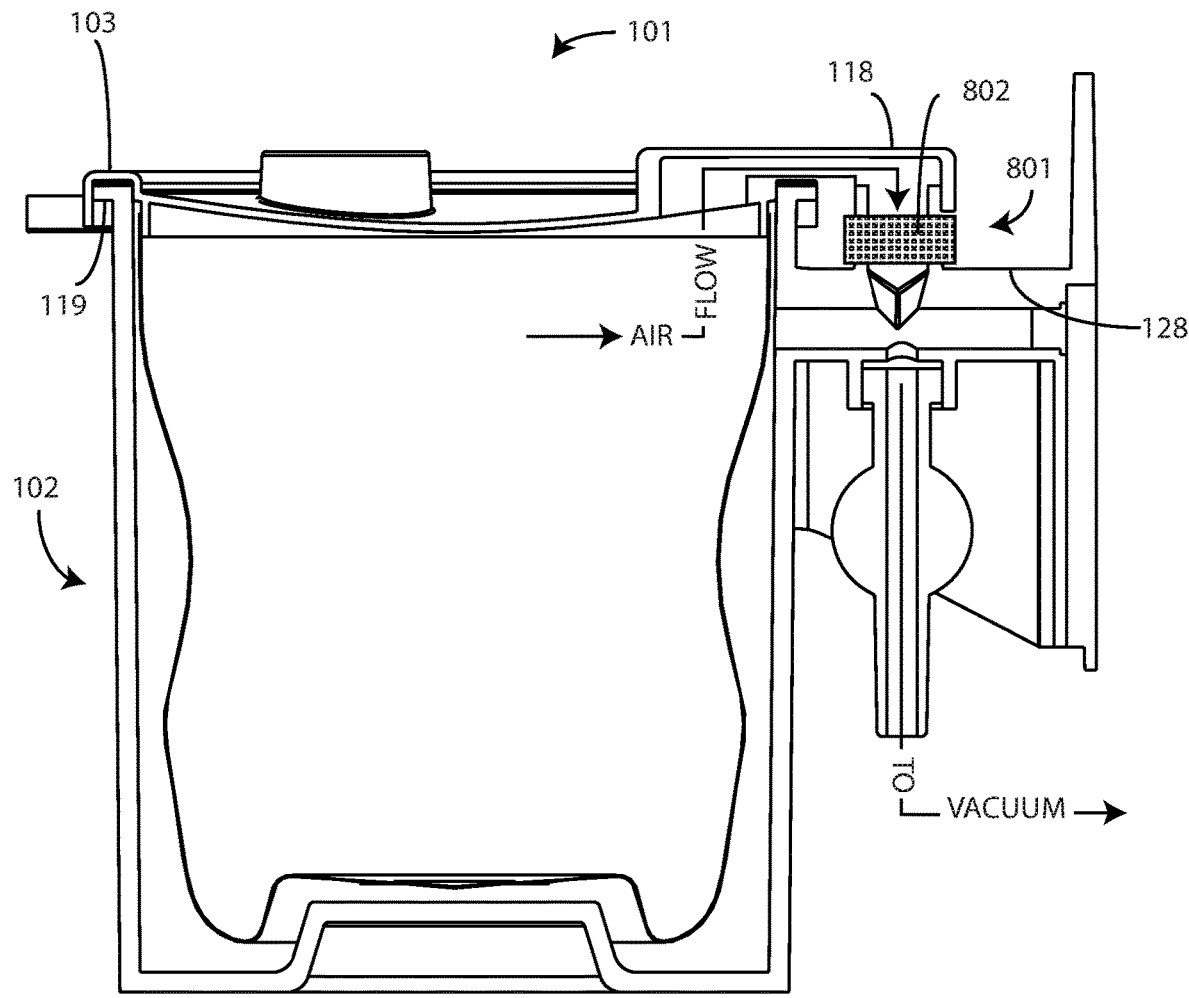
FIG. 8 illustrates a sectional view of another explanatory canister system in accordance with one or more embodiments of the disclosure.

Turning now to FIG. 8, illustrated therein is yet another valve 801 configured in accordance with one or more embodiments of the disclosure. As was the case with the valves (601,701) of FIGS. 6-7, the valve 801 of FIG. 8 is disposed atop the mechanical support 128. As shown in FIG. 8, when the canister lid 101 is attached to the canister 102, the valve 801 is disposed between the second lobe 118 extending from the annular perimeter 103 when the canister lip engaging recess of the annular perimeter 103 engages the lip 119 of the canister 102. This allows the twist mechanism 802 to be accessed from beneath the canister lid (101).

As was the case with the valves (601,701) of FIGS. 6-7, the valve 801 of FIG. 8 is equipped with a twist mechanism 802. The twist mechanism 802 can include visual indicia and/or words to easily indicate to a user whether the valve 801 is ON or OFF. By twisting the twist mechanism 802 to one of the right or the left, the valve 801 is turned ON. By twisting the twist mechanism 802 to another of the right or the left, the valve 801 is turned OFF.

Figure 9:
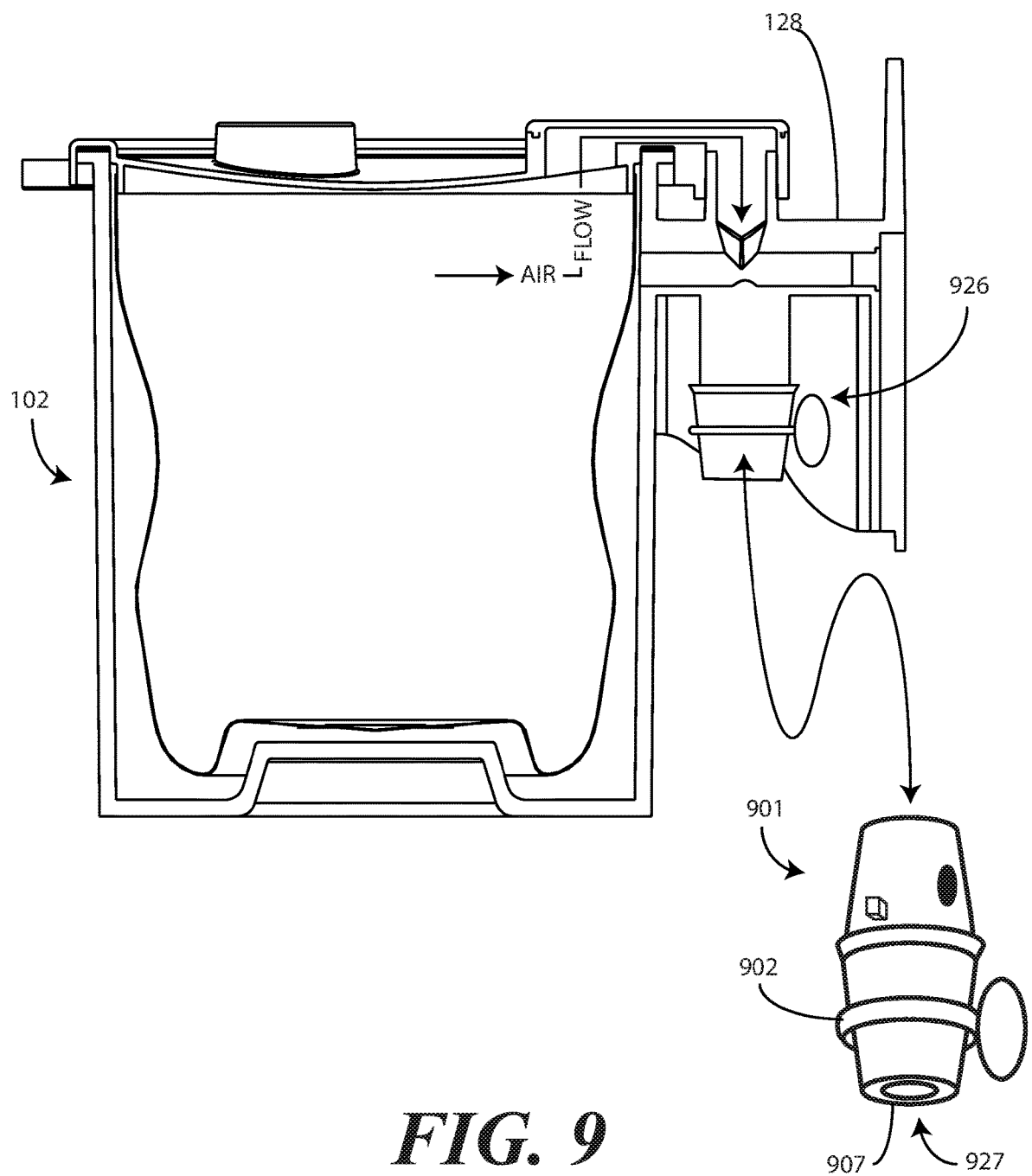
FIG. 9 illustrates a sectional view of still another explanatory canister system in accordance with one or more embodiments of the disclosure.

Turning now to FIG. 9, illustrated therein is yet another valve 901 configured in accordance with one or more embodiments of the disclosure. In contrast with the valves (601,701,801) of FIGS. 6-8, the valve 901 of FIG. 9 is disposed beneath the mechanical support 128. Accordingly, the valve 901 corms part of an exterior suction assembly 926 extending downward from the mechanical support 128 and terminating at a suction port 927. When the suction port 927 is attached to a central vacuum or suction apparatus in a hospital or other medical facility, and the twist mechanism 902 is rotated to the ON position, the conduit 907 defined through the valve 901 permits the central vacuum or suction apparatus to draw air from the interior of the canister 102. As was the case with the embodiment of FIG. 7, and optionally FIGS. 4-6, the valve 901 of FIG. 9 is removable from the canister 102 for cleaning or replacement.

Figure 10:
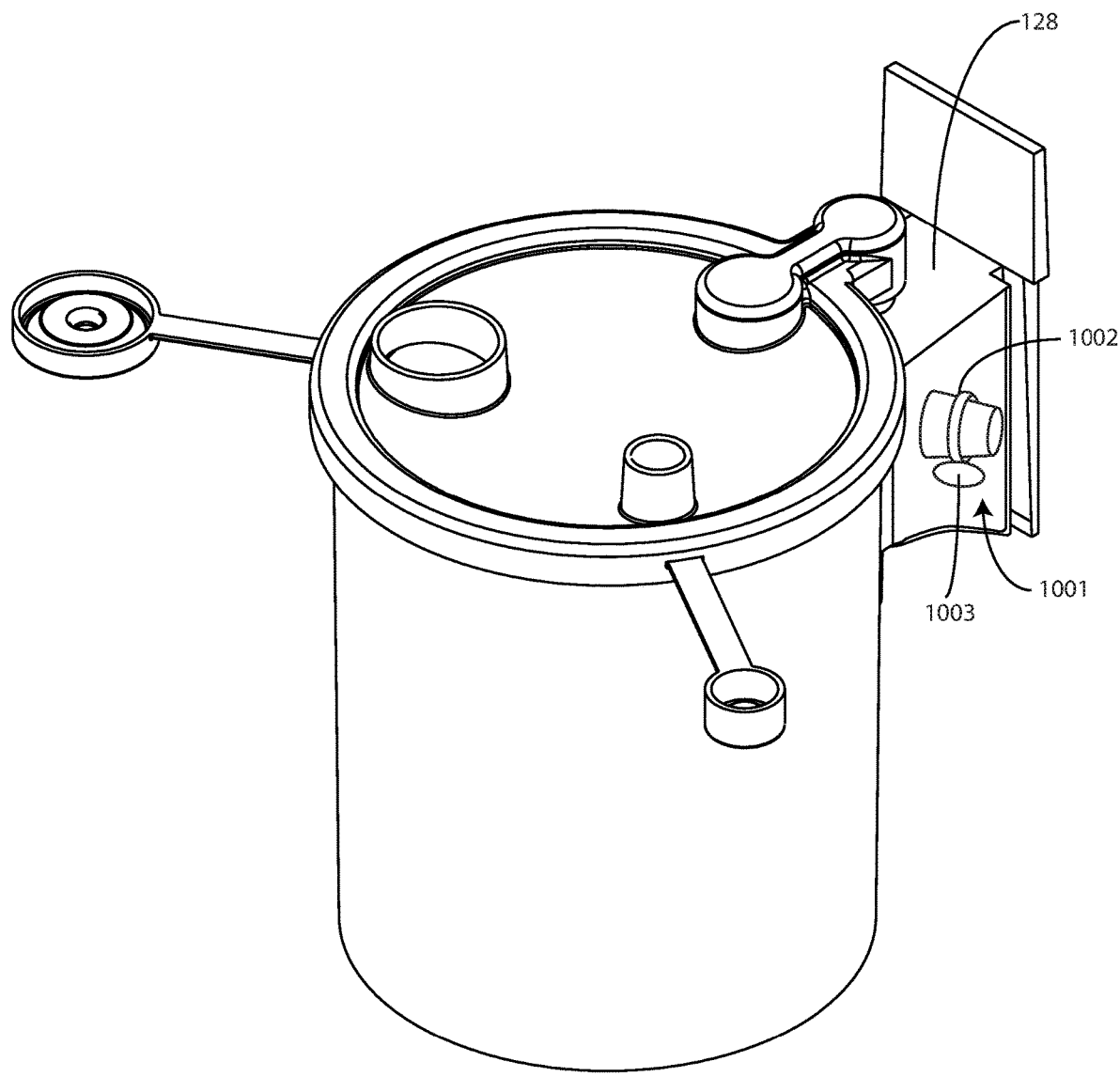
FIG. 10 illustrates a perspective view of yet another explanatory canister system in accordance with one or more embodiments of the disclosure.

Turning now to FIG. 10, illustrated therein is yet another valve 1001 configured in accordance with one or more embodiments of the disclosure. As was the case with FIG. 1, in this illustrative embodiment an exterior suction assembly extends downward from the mechanical support 128 and terminates at a suction port. The suction port can attach to a central vacuum or suction apparatus in a hospital or other medical facility. In this illustrative embodiment, rather than being equipped with a large, bulky, and unwieldy mechanical valve switch (129), the valve 1001 has a simple twist mechanism 1002 coupled to a paddle 1003. By applying force to the paddle 1003 to twist the twist mechanism 1002 to one of the right or the left, the valve 1001 is turned ON. By applying an opposite force to the paddle 1003 to twist the twist mechanism 1002 to the other of the right or the left, the valve 1001 is turned OFF. The valve 1001 offers a more streamlined, compact, easy to use, and more aesthetically pleasing control mechanism than did the large, bulky, and unwieldy mechanical valve switch (129) of FIG. 1.

As noted above, the use of the canister lid 101 in FIGS. 1-10 helps to eliminate at least one hose or tubing compared with prior art designs. Specifically, the canister lid 101 includes the suction conduit (112), which is hollow on the inside such that air or other fluid can be drawn through each of the first lobe (117), the suction conduit (112), and the second lobe 118. As the suction conduit (112) is disposed between the first lobe (117) and the second lobe (118) is hollow and connects these two chambers, air and other fluids can flow through the suction conduit (112). Thus, the inclusion of the suction conduit (112) advantageously allows for the elimination of a hose or tube that would traditionally be used to remove air from, or deliver air to, a suction canister.

At the same time, the embodiments of FIGS. 1-10 all include some form of exterior suction assembly (e.g., exterior suction assembly 126 of FIG. 1) that has a vacuum tube input (e.g., vacuum tube input 123 of FIG. 1) that is coupled to a hose or tube. In the embodiments of FIGS. 1-10, this vacuum tube input extends downward from the mechanical support extending from the canister body, and allows the embodiments of FIGS. 1-10 to be used with prior art stands and hospital infrastructure where a vacuum hose connection is provided.

Figure 11:
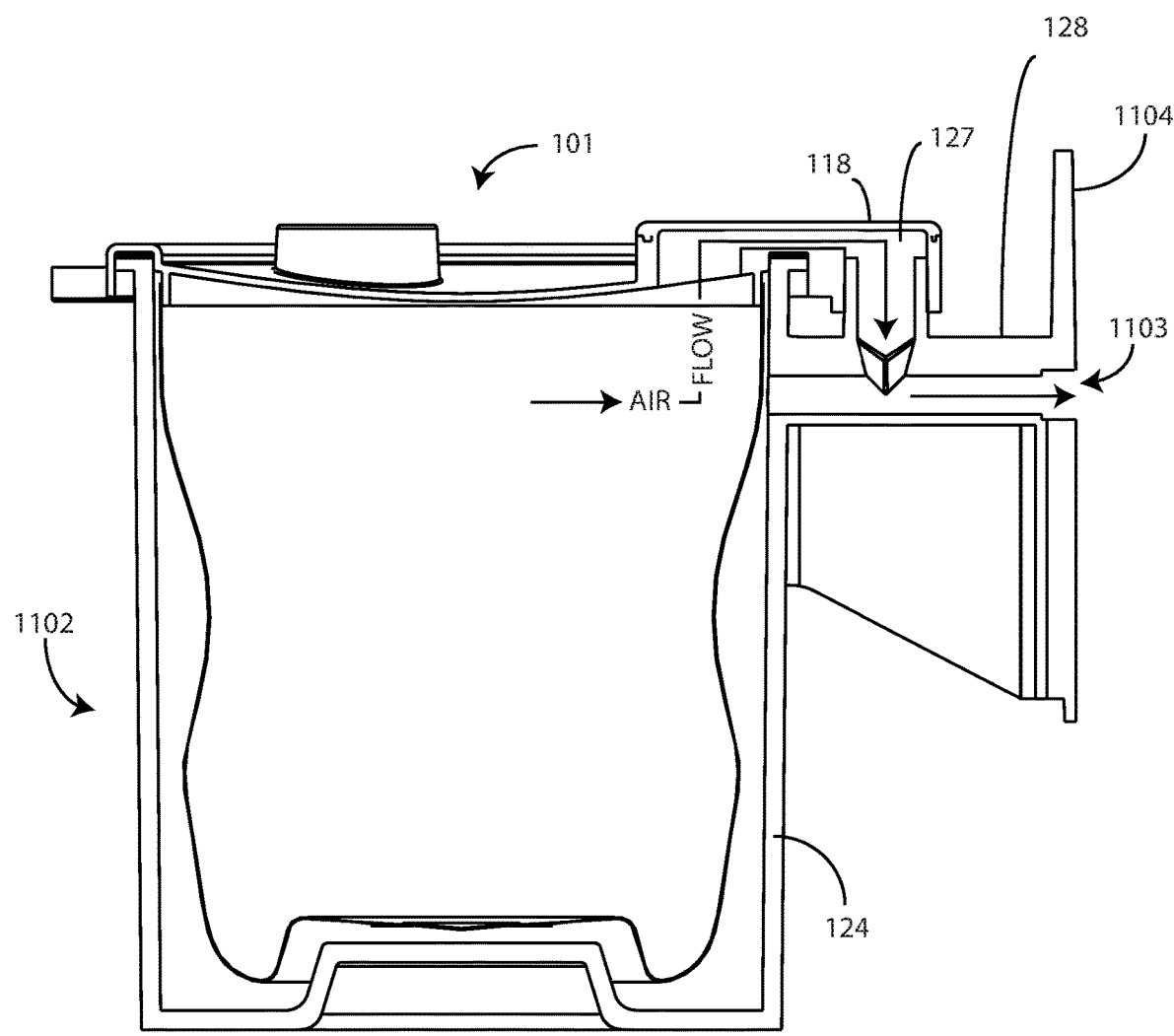
FIG. 11 illustrates another explanatory canister system in accordance with one or more embodiments of the disclosure.

However, embodiments of the disclosure contemplate that additional hoses or vacuum tubes can further be eliminated from a suction system. Turning now to FIG. 11, illustrated therein is one such suction canister. In FIG. 11, rather than including a vacuum tube input, the canister 1102 includes a tubeless vacuum connection port 1103 that couples to a tubeless manifold. One example of such a tubeless manifold is described below with reference to FIG. 12.

Effectively, the embodiment of FIG. 11 differs from previous embodiments in that the tubeless vacuum connection port 1103 extends laterally through a mounting bracket 1104 extending orthogonally from the mechanical support 128 that extends distally from the cylindrical sidewall 124 of the canister 1102. This is in contrast to the vacuum tube input (123) of FIG. 1, which extends downward from the mechanical support. Accordingly, in the illustrative embodiment of FIG. 11, the tubeless vacuum connection port 1103 extends from the suction port 127 toward, and away from, the cylindrical sidewall 124 of the canister 1102.

As shown in FIG. 11, the second lobe 118 of the canister lid 101 engages the suction port 127 of the canister 1102 when the annular perimeter of the canister lid 101 engages the lip 119 of the canister 1102. When the canister lid 101 is sealed to the canister 1102, and a vacuum source is coupled to the tubeless vacuum connection port 1103, air and/or fluids are drawn both through the tubeless vacuum connection port 1103 and the suction port 127 to draw fluids from the disposable liner 304 without collapsing the same.

Figure 12:
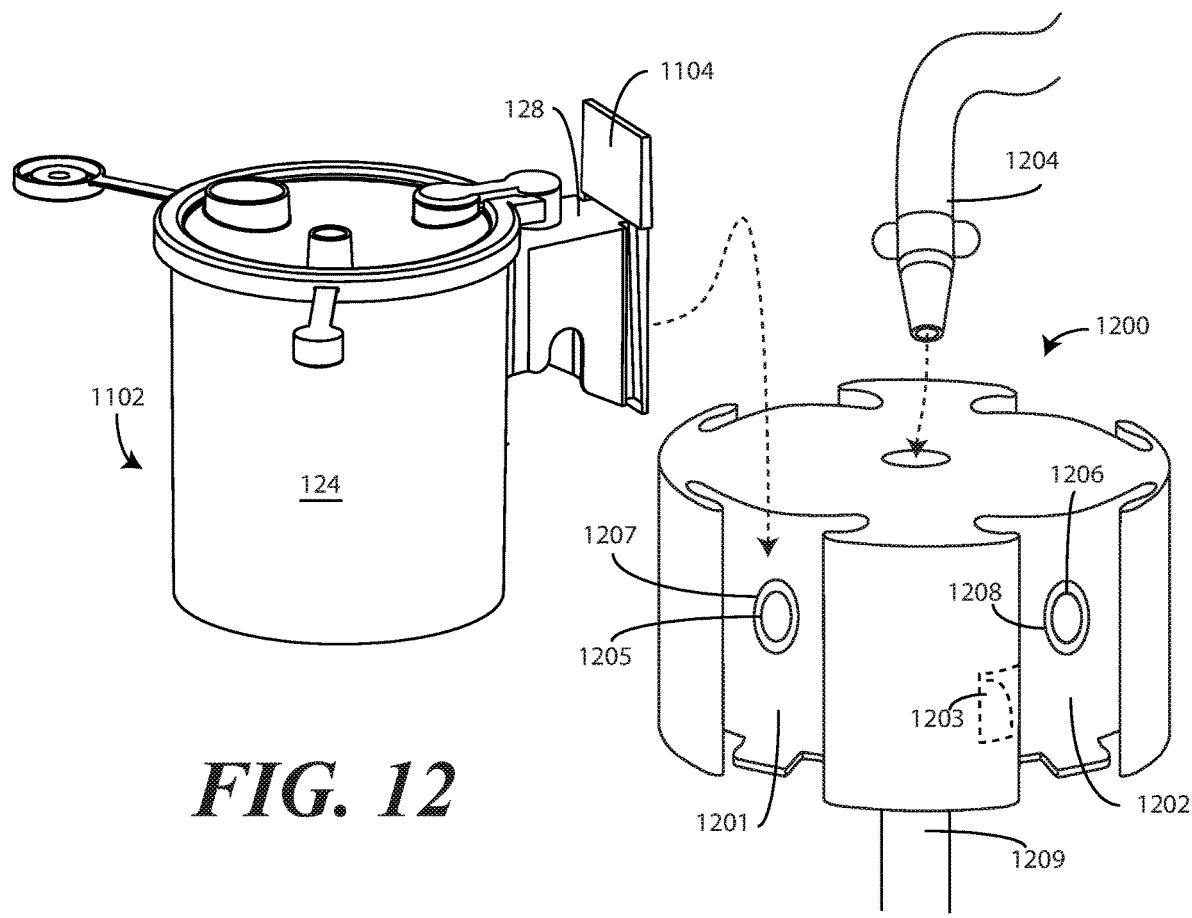
FIG. 12 illustrates another explanatory canister system in accordance with one or more embodiments of the disclosure.

Turning now to FIG. 12, illustrated therein is the canister 1102 being coupled to a hub mount vacuum source 1200. In one embodiment, the hub mount vacuum source 1200 is manufactured from plastic and is circular in its plan view to accommodate many different canisters. However, as will be shown in subsequent figures, other hub mount vacuum sources can take different plan cross sectional shapes.

In this illustrative embodiment, the hub mount vacuum source 1200 includes one or more canister receivers 1201, 1202 to receive the mounting bracket 1104 of the canister 1102 that extends orthogonally from the mechanical support 128 that extends distally from the cylindrical sidewall 124 of the canister 1102. In one or more embodiments, the mounting bracket 1104 of the canister 1102 is pressure-fit into each canister receiver 1201,1202 using gasket compression and draft angles of the sidewalls of each canister receiver 1201, 1202. In one or more embodiments, each canister receiver 1201,1202 can include an internal locking mechanism 1203 that retains the mechanical support 128 securely in a predefined alignment within its respective canister receiver 1201.

As shown in FIG. 12, in one embodiment each canister receiver 1201,1202 includes a vacuum port 1205,1206 that aligns with the tubeless vacuum connection port (1103) extending laterally through a mounting bracket 1104 when the mounting bracket 1104 seats within its respective canister receiver 1201. A central vacuum source 1204 can be coupled to the hub mount vacuum source 1200 to provide suction to teach of the vacuum ports 1205,1206 when activated. The central vacuum source 1204 can propagate to other hub mount vacuum sources, as necessary, via internal piping 1209 or other connections. While shown connected to the top of the hub mount vacuum source 1200 in FIG. 12, in other embodiments the central vacuum source 1204 can be coupled to the bottom of the hub mount vacuum source 1200 in a central location or off-center location. In one embodiment, the central vacuum source 1204 is permanently coupled to the hub mount vacuum source 1200. In other embodiments, the central vacuum source 1204 may be detachable from the hub mount vacuum source 1200 for optional regular attachment thereto.

Figure 14:
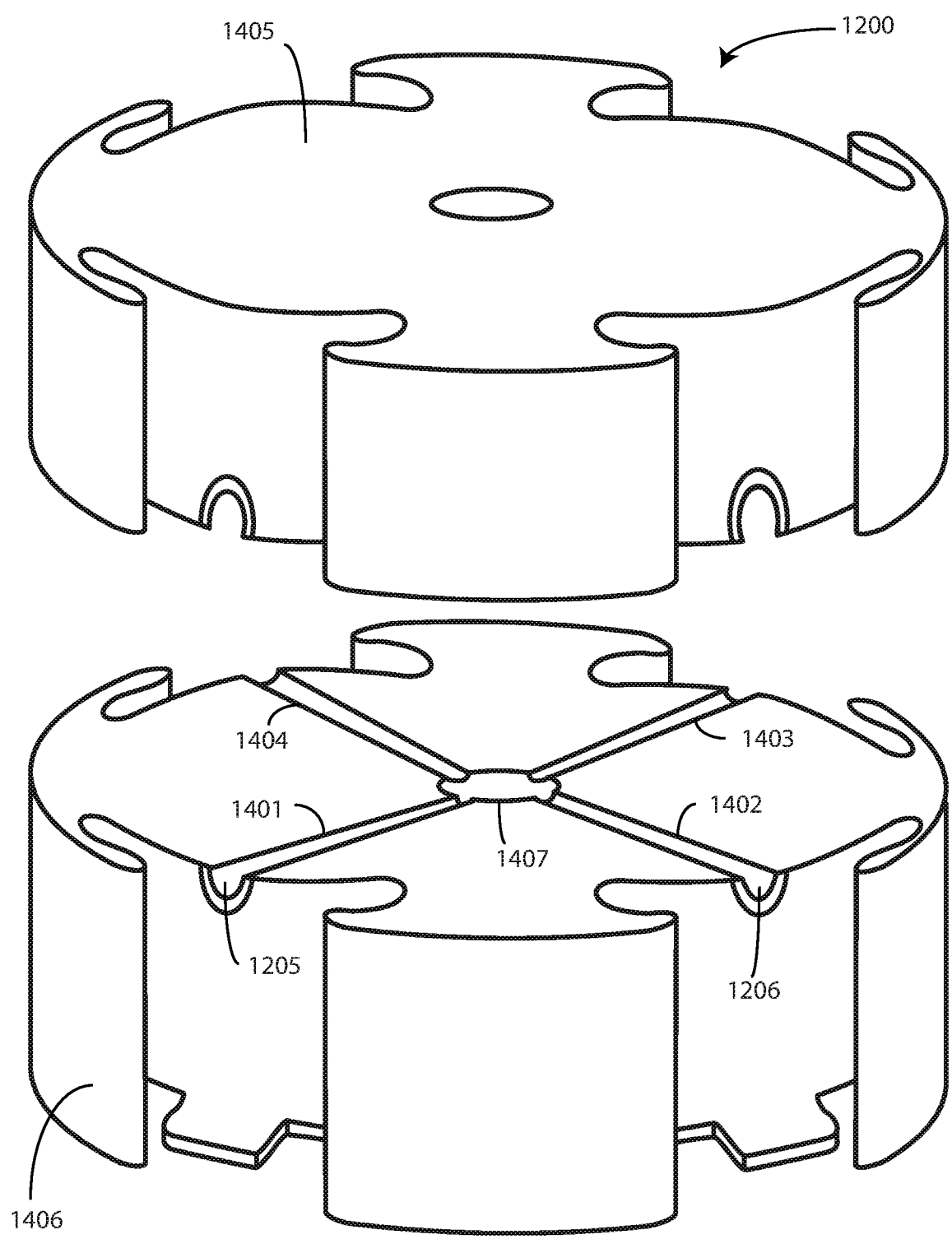
FIG. 14 illustrates an exploded view of one explanatory canister stand in accordance with one or more embodiments of the disclosure.

In one or more embodiments, vacuum pressure flows from the vacuum ports 1205,1206 to the central vacuum source 1204 through internal manifolds disposed within the hub mount vacuum source 1200. Turning briefly to FIG. 14, such internal manifolds 1401,1402,1403,1404 can be seen.

In the illustrative embodiment of FIG. 14, the hub mount vacuum source 1200 is configured in two portions, i.e., a first portion 1405 and a second portion 1406. In one embodiment, the first portion 1405 is separable from the second portion 1406 to clean or otherwise service the internal manifolds 1401,1402,1403,1404. In this illustrative embodiment, the vacuum ports 1205,1206 split in two partial port portions when the first portion 1405 and the second portion 1406 are separated to facilitate cleaning or other service operations. In one or more embodiments, gaskets can be placed in, or along side, the internal manifolds 1401,1402,1403,1404 to prevent air leaks between manifolds when the first portion 1405 is coupled to the second portion 1406. In one or more embodiments, each of the first portion 1405 and the second portion 1406 are manufactured from thermoplastics with an injection molding process.

In the illustrative embodiment of FIG. 14, each of the internal manifolds 1401,1402,1403,1404 terminates at a central vacuum aperture 1407. In one embodiment, when the first portion 1405 couples to the second portion 1406, the central vacuum aperture 1407 disposed in the second portion 1406 can couple to the corresponding central vacuum aperture disposed in the first portion 1405 with a threaded connection to provide a hermetic seal. Additionally, it should be noted that the first portion 1405 can be coupled to the second portion 1406 in a variety of ways, including by using clamps, latches, a threaded central column, pressure fitting with screws, or with mechanical components that snap together. Other mechanisms for coupling either the first portion 1405 to the second portion 1406 or the central vacuum aperture 1407 disposed in the second portion 1406 to the corresponding central vacuum aperture disposed in the first portion 1405 will be obvious to those of ordinary skill in the art having the benefit of this disclosure.

While the internal manifolds 1401,1402,1403,1404 of FIG. 14 are shown as mechanical recesses in the first portion 1405 and second portion 1406, respectively, in other embodiments these manifolds can comprise removable manifold tubing that can be detached from each vacuum port 1205,1206 for cleaning or replacement. Other configurations of internal manifolds 1401,1402,1403,1404 will be obvious to those of ordinary skill in the art having the benefit of this disclosure.

Turning now back to FIG. 12, in one or more embodiments, O-ring seals 1207,1208 or other sealing mechanisms can be disposed about the vacuum ports 1205,1206 to ensure that there is a pressure-fit seal between the tubeless vacuum connection port (1103) and its corresponding vacuum port 1205. Accordingly, when the central vacuum source 1204 is actuated, fluids can be drawn from the tubeless vacuum connection port (1103) through the vacuum ports 1205,1206 through the internal manifolds 1401,1402,1403,1404 into the central vacuum source 1204.

Figure 13:
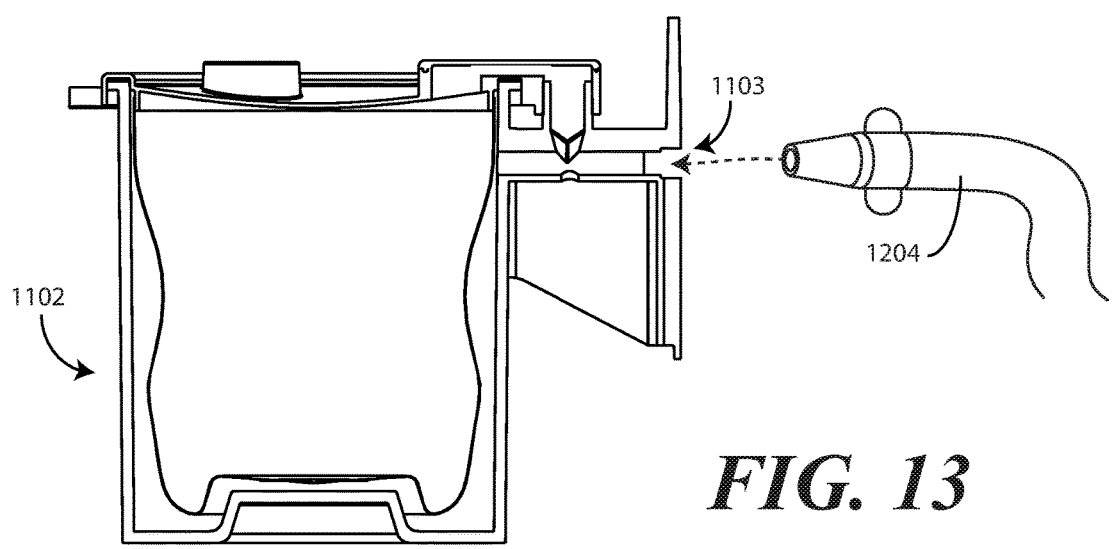
FIG. 13 illustrates another explanatory canister system in accordance with one or more embodiments of the disclosure.

In one or more embodiments, the tubeless vacuum connection port (1103) can be configured so that the canister 1102 can be used with either a hub mount vacuum source 1200 or a prior art tube. For example, turning now to FIG. 13 illustrated therein is the central vacuum source 1204 being inserted directly into the tubeless vacuum connection port 1103 so that the canister 1102 can be used without the hub mount vacuum source 1200. Where the central vacuum source 1204 is too large for, or is otherwise non-fitting with, the tubeless vacuum connection port 1103, a separate suction hose can be pressure fit into the tubeless vacuum connection port 1103 so that the canister 1102 can be used in a standalone mode.

Figure 21:
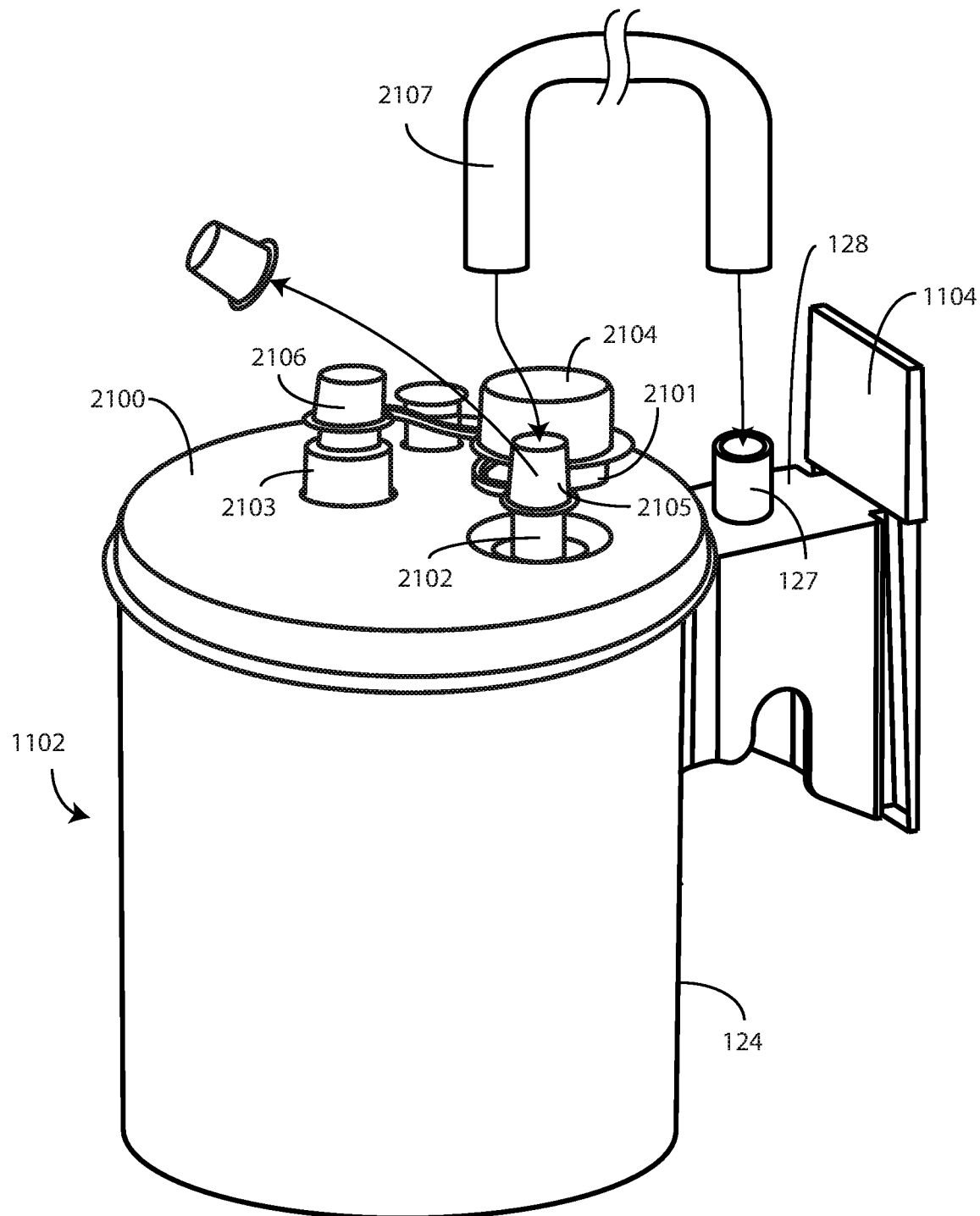
FIG. 21 illustrates a prior art lid on a canister configured in accordance with one or more embodiments of the disclosure.

Moreover, embodiments of the disclosure can even be used with prior art lids. Turning briefly to FIG. 21, illustrated therein is a prior art lid 2100 being used with a canister 1102 configured in accordance with one or more embodiments of the disclosure. The prior art lid includes a pour spout 2101, and one or more suction ports 2102,2013. In this illustrative embodiment, each of the pour spout 2101 and the suction ports 2102,2013 includes a cap 2104,2105,2016 that can be used as a cover when tubing 2107 is not coupled thereto.

As was the case with FIG. 11, the canister 1102 includes a tubeless vacuum connection port (1103) that couples to a tubeless manifold. The tubeless vacuum connection port (1103) extends laterally through a mounting bracket 1104 extending orthogonally from the mechanical support 128 that extends distally from the cylindrical sidewall 124 of the canister 1102. Rather than a second lobe (118) of a canister lid (101) configured in accordance with embodiments of the disclosure engaging the suction port 127 of the canister 1102, to make the prior art lid 2100 compatible with the canister 1102 tubing 2107 can be coupled between, for example, the suction port 127 of the canister 1102 and a corresponding suction port 2102 of the lid 2100. When the prior art lid 2101 is sealed to the canister 1102, and a vacuum source is coupled to the tubeless vacuum connection port (1103), air and/or fluids are drawn both through the tubeless vacuum connection port (1103) and the suction port 127, through the tubing 2107 and through the lid's suction port 2102 to draw fluids from canister 1102.

Figure 15:
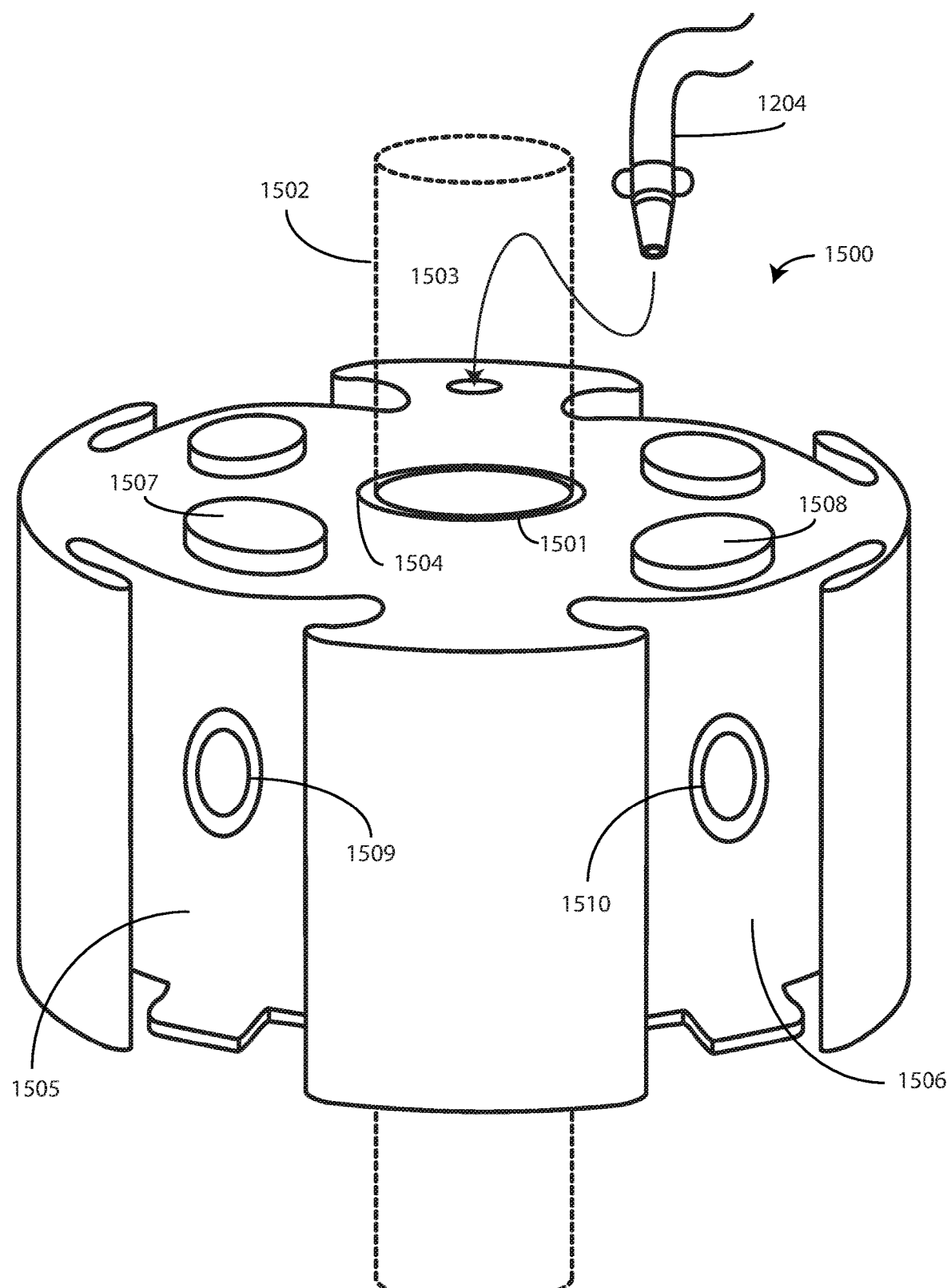
FIG. 15 illustrates a perspective view of another explanatory canister stand in accordance with one or more embodiments of the disclosure.

Turning now to FIG. 15, illustrated therein is an alternate hub mount vacuum source 1500 configured in accordance with one or more embodiments of the disclosure. In one or more embodiments the hub mount vacuum source 1500 can be equipped with a central aperture 1501 so that it can be mounted to a pole 1502 or stand. Where such a central aperture 1501 is included, the connection 1503 for the central vacuum source 1204 can be moved to a non-central location on the top, the bottom, or the sides of the hub mount vacuum source 1500. In one or more embodiments, a locking mechanism 1505 can also be positioned about the central aperture 1501 to securely retain the hub mount vacuum source 1500 to the pole 1502 or stand. While the locking mechanism 1505 is shown on the top of the hub mount vacuum source 1500 in FIG. 15, it can also be disposed along the bottom as well.

Figure 16:
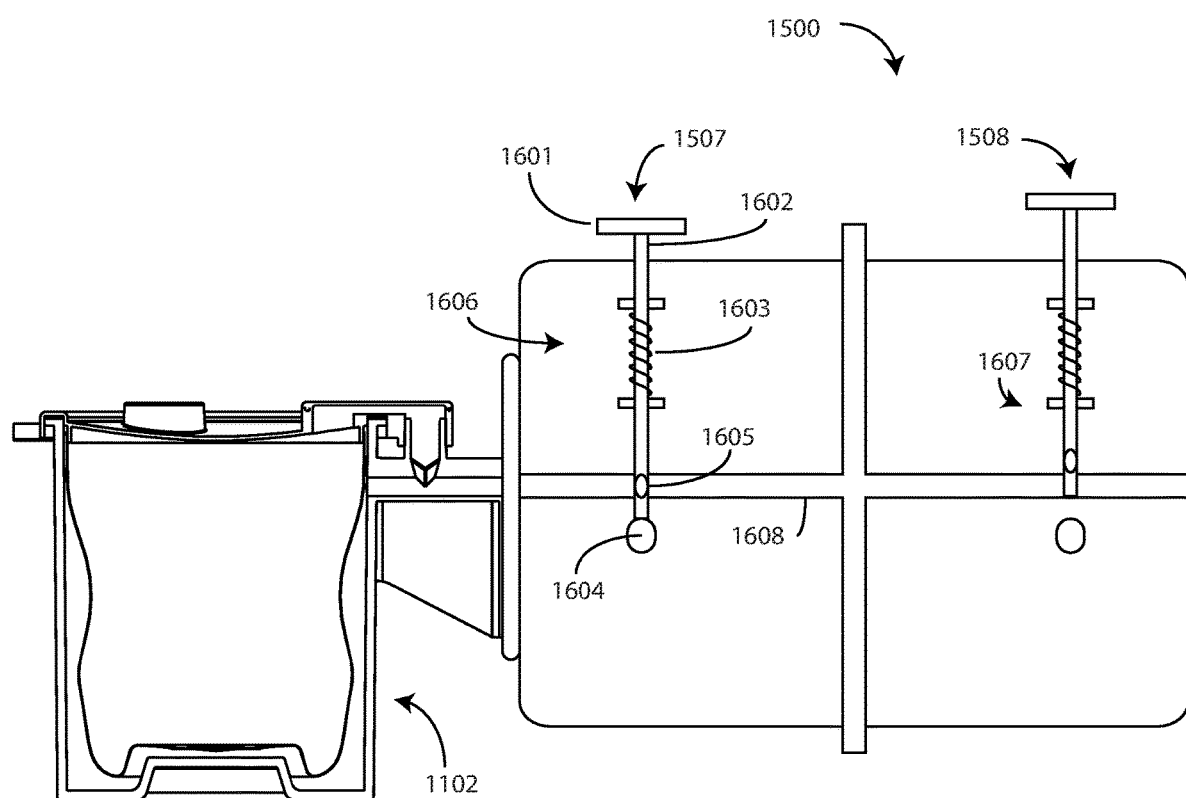
FIG. 16 illustrates a sectional view of another explanatory canister system in accordance with one or more embodiments of the disclosure.

In the illustrative embodiment of FIG. 15, each canister receiver 1506 has a corresponding actuation switch 1507, 1508 that allows each individual vacuum port 1509,1510 to be turned ON or OFF. Turning now to FIG. 16, illustrated therein is a sectional view of the hub mount vacuum source 1500 showing the internal components of each actuation switch 1507,1508.

In one or more embodiments, each actuation switch 1507,1508 comprises a push button 1601, a shaft 1602, a spring 1603, an aperture 1605 disposed along the shaft 1602, and a pen click mechanism 1604. When the push button 1601 is pressed into the hub mount vacuum source 1500, the pen click mechanism 1604 retains the shaft 1602 in a first position 1606 with the aperture 1605 aligned with the internal manifold 1608 to allow air and fluids to flow therethrough. A second press of the push button 1601 causes the pen click mechanism 1604 to release the shaft 1602 from the first position 1606 to a second position 1607 where airflow is blocked. Accordingly, each canister 1102 is "activated" by depressing the push button 1601, and airflow can be allowed or prevented through each internal manifold 1608 using the actuation switch 1507.

Figure 17:
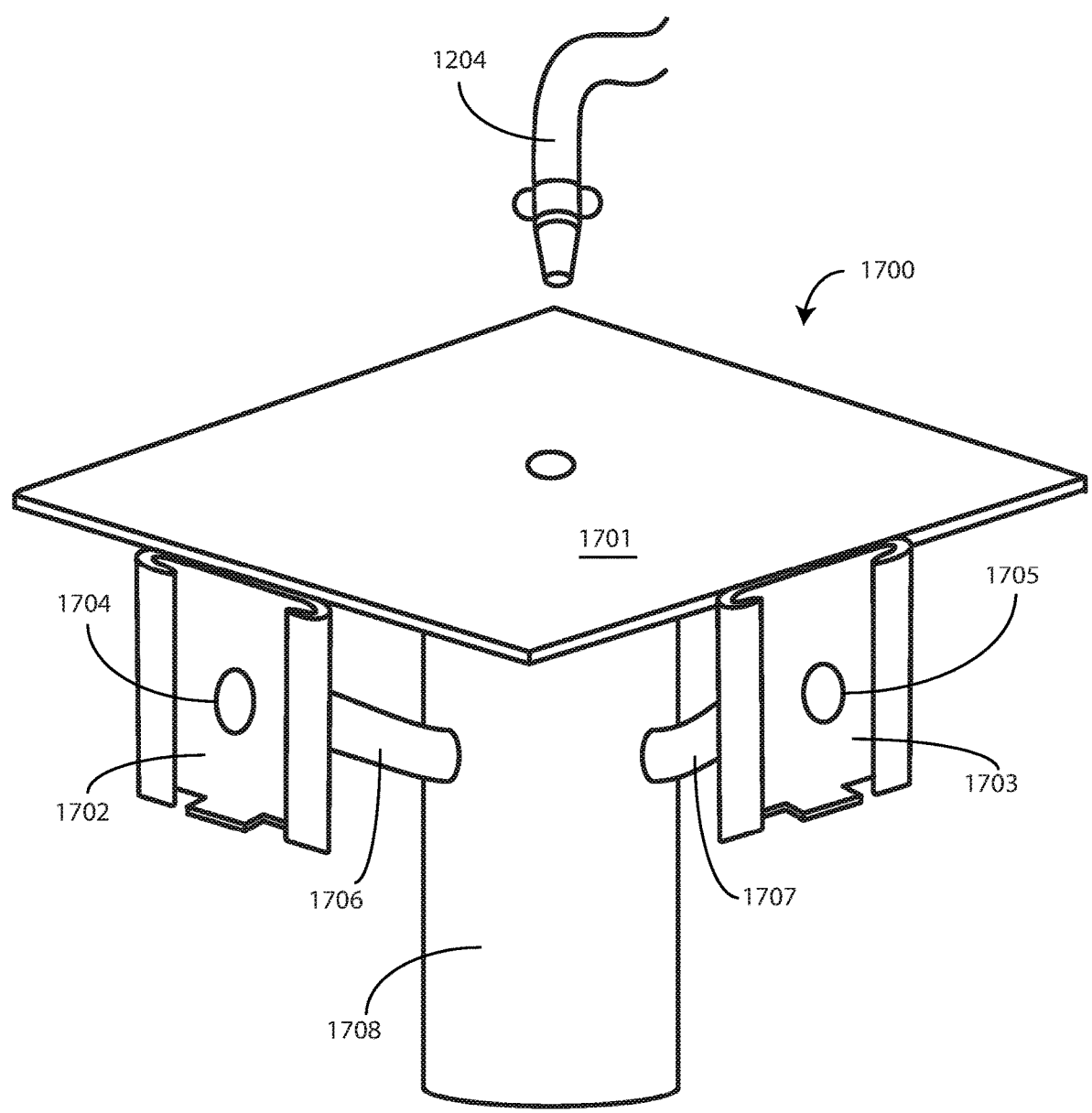
FIG. 17 illustrates a perspective view of another explanatory canister stand in accordance with embodiments of the disclosure.

Turning now to FIG. 17, illustrated therein is an alternate hub mount vacuum source 1700 configured in accordance with one or more embodiments of the disclosure. As shown in FIG. 17, rather than having a closed body, the hub mount vacuum source 1700 is defined by a flat surface 1701 that can be used as a small table or work surface. While the flat surface 1701 is square in FIG. 17 so as to hold four canisters, it can take other shapes as well. In another embodiment, the flat surface 1701 is hexagonal so as to connect to six canisters. In another embodiment, the flat surface 1701 is octagonal so as to connect to eight canisters. Other shapes and configurations for the flat surface 1701 will be obvious to those of ordinary skill in the art having the benefit of this disclosure. In one embodiment, the flat surface 1701 is manufactured from stainless steel, and has its diameter minimized to deliver a reduced footprint on the hospital floor. In one embodiment, the flat surface 1701 can be mounted on a pole 1708 or other stand, which can be adjustable in height.

In the illustrative embodiment of FIG. 17, one or more canister receivers 1702,1703 are manufactured by bending pieces of stainless steel and welding them to the flat surface 1701. As with the hub mount vacuum source (1200) of FIG. 12, each canister receiver 1702,1703 is configured to receive the mounting bracket (1104) of a canister (1102). The mounting bracket (1104) of the canister (1102) can be pressure-fit into each canister receiver 1702,1703 using gasket compression and draft angles as described above.

Each canister receiver 1702,1703 includes a vacuum port 1704,1705 that aligns with the tubeless vacuum connection port (1103) when the mounting bracket 1104 seats within its respective canister receiver 1702. A central vacuum source 1204 can be coupled to the hub mount vacuum source 1700 to provide suction to teach of the vacuum ports 1704,1705 through one or more external manifolds 1706,1707. In one or more embodiments, vacuum pressure flows from the vacuum ports 1205,1206 to the central vacuum source 1204 through internal manifolds disposed within the hub mount vacuum source 1200. Turning briefly to FIG. 14, such internal manifolds 1401,1402,1403,1404 can be seen.

Figure 18:
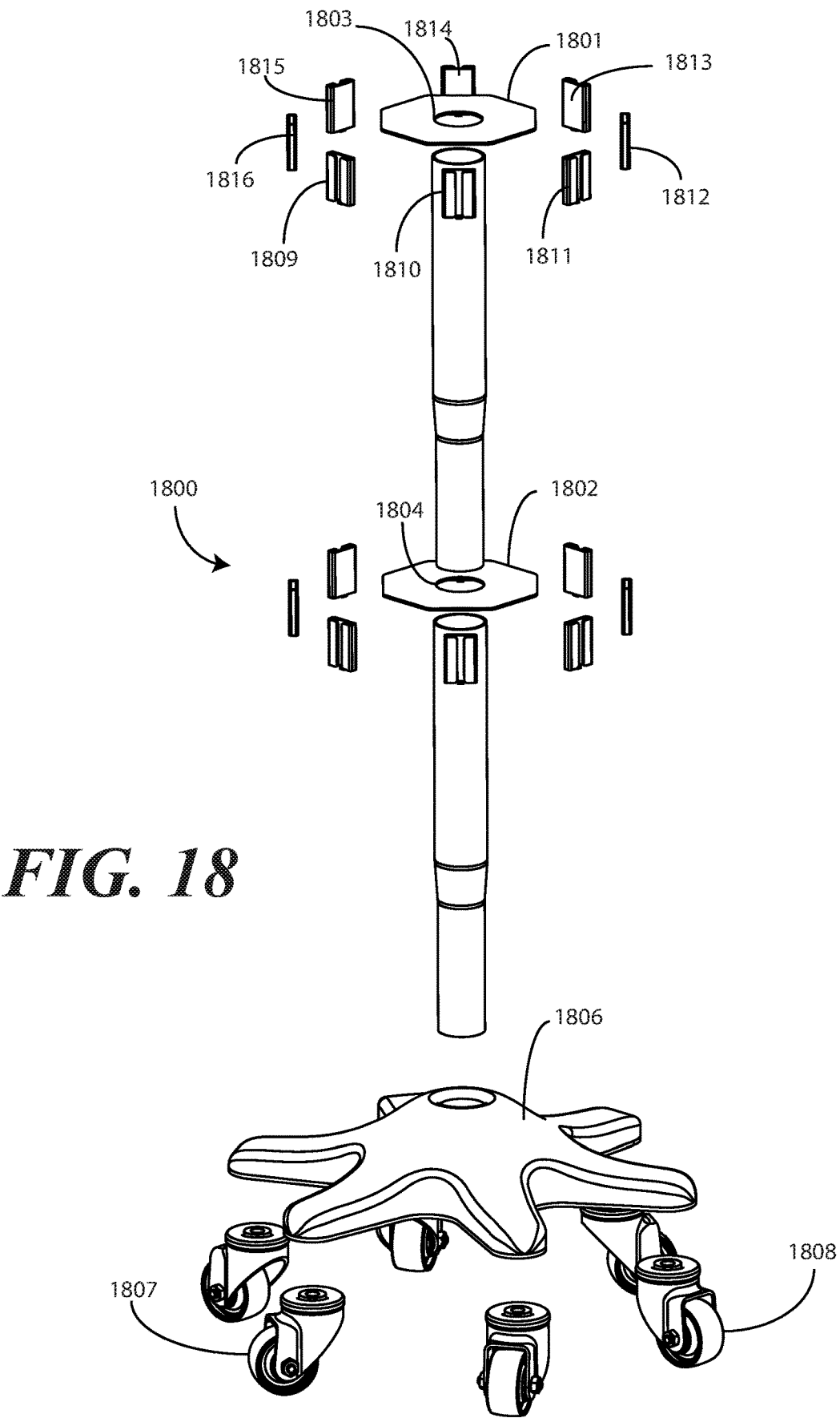
FIG. 18 illustrates a perspective view of another explanatory canister stand in accordance with embodiments of the disclosure.

Turning now to FIG. 18, illustrated therein is a hub mount stand 1800, to which one or more canisters configured in accordance with one or more embodiments of the disclosure can be coupled. The illustrative hub mount stand 1800 of FIG. 18 includes one or more flat surfaces 1801,1802 that function as did the flat surface (1701) of FIG. 17. In this illustrative embodiment, each flat surface 1801,1802 includes a central aperture 1803,1804 so that the flat surfaces 1801,1802 can be mounted to a central column 1805. The central column 1805 is coupled to a base 1806 that is supported by one or more casters 1807,1808.

In the illustrative embodiment of FIG. 18, each flat surface 1801,1802 is octagonal. Accordingly, eight mounting brackets configured as canister receivers 1809,1810, 1811,1812, 1813,1814,1815,1816 can be coupled to each flat surface 1801,1802 so that eight canisters can be coupled to each flat surface 1801,1802.

Figure 19:
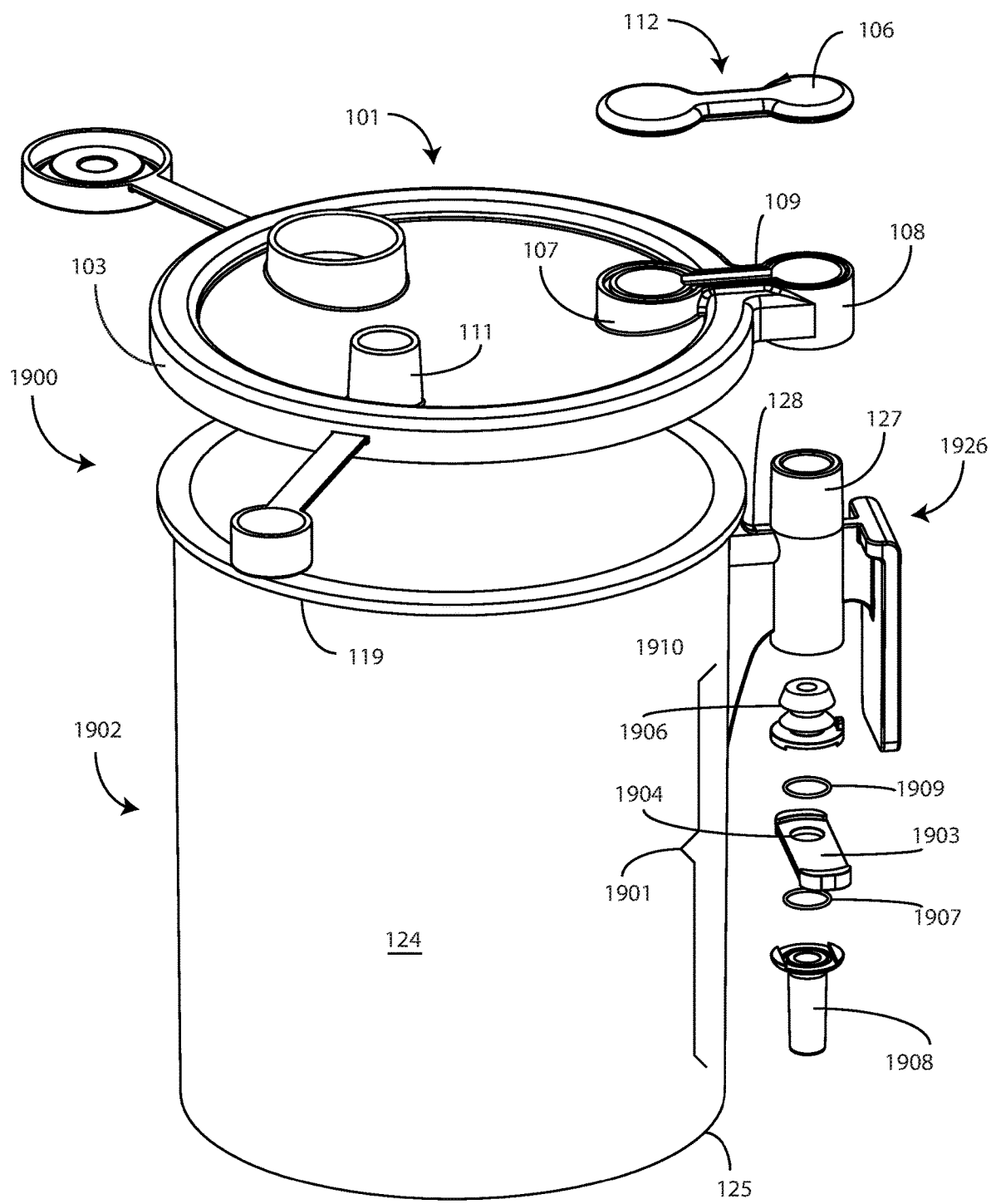
FIG. 19 illustrates a perspective view of another explanatory canister system in accordance with embodiments of the disclosure.

Turning now to FIG. 19, illustrated therein is one explanatory canister system 1900 suitable for use with the hub mount stand (1800) of FIG. 18. As with previous embodiments, the canister system 1900 includes a canister lid 101 and a canister 1902. A disposable liner (not shown) can be attached to the canister lid 101 to catch fluids or other materials drawn in through the suction port 111.

As before, a suction conduit 112 comprises a separate suction conduit cap 106 that adhesively sealed to each of a first lobe annular wall 107, the second lobe annular wall 108, and the one or more suction duct sidewalls 109 in one embodiment. The suction conduit 112 comprises a suction duct defined by the suction duct sidewalls 109, a first lobe annular wall 107, and the second lobe annular wall 108. The suction conduit 112 again resembles a dog bone or double-ended lollipop. The suction conduit 112 is hollow on the inside such that air or other fluid can be drawn through the suction conduit 112. The inclusion of the suction conduit 112 advantageously allows for the elimination of a hose or tube that would traditionally be used to remove air from, or deliver air to, a suction canister.

The annular perimeter 103 of the canister lid 101 is operable to connect to the lip edge 119 of the canister 1902. The canister 1902 includes a cylindrical sidewall 124 that extends from a base 125. In this illustrative embodiment, the canister 1902 also includes an exterior suction assembly 1926. The exterior suction assembly 1926 includes a suction port 127 extending distally from the cylindrical sidewall 124 on a mechanical support 128 that allows the suction port 127 to attach to a central vacuum or suction apparatus in a hospital or other medical facility through a detachable valve 1901.

The detachable valve 1901 of FIG. 19 is similar to the valve (901) of FIG. 9 in that it is disposed beneath the mechanical support 128. It is also similar to the valve (501) of FIG. 5 in that it comprises a plank 1903 as an actuation mechanism. The plank 1903 includes an aperture 1904 that aligns with the conduit 1905 defined axially in the valve 1901 when the plank 1903 is in a first position. However, when the plank 1903 is translated laterally to a second position, the aperture 1904 becomes misaligned with the conduit 1905 to prevent the flow of air.

In this illustrative embodiment, the plank 1903 is disposed between two O-ring seals 1906,1907. The plank 1903 and O-ring seals 1906,1907 are then disposed between a vacuum connection nozzle and a rubber valve insert 1909 that allows the valve 1901 to be removably inserted into a valve receiver 1910 disposed beneath the mechanical support 128. Accordingly, the valve 1901 can selectively be removed from the canister 1902 for cleaning, replacement or service.

Figure 20:
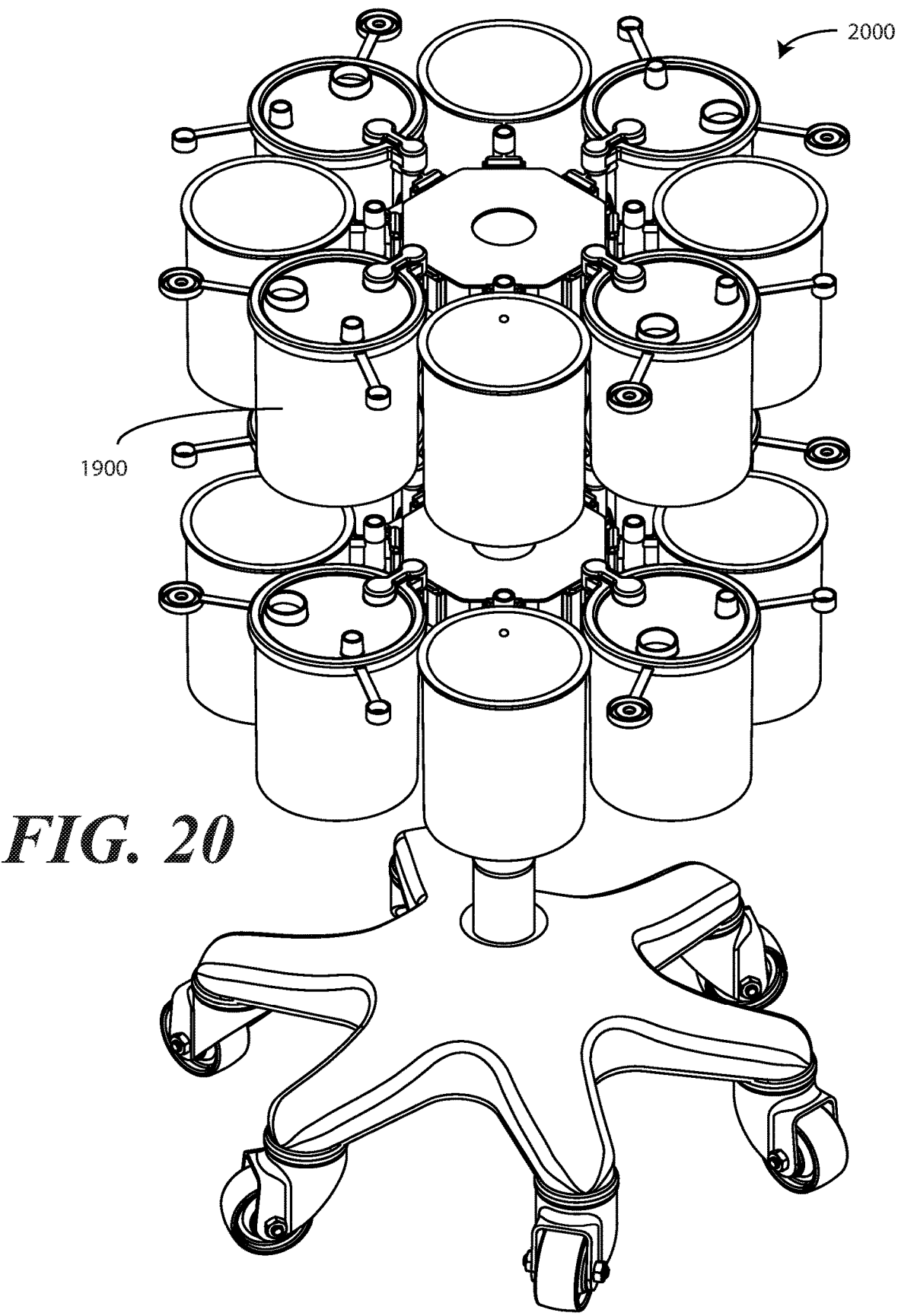
FIG. 20 illustrates a perspective view of another explanatory canister system in accordance with embodiments of the disclosure.

Once the canister is assembled, it can be attached to the hub mount stand (1800) of FIG. 19. As shown in FIG. 20, a completed suction canister system 2000 can include up to sixteen canister systems 1900 for maximum sucking potential.

Figure 22:
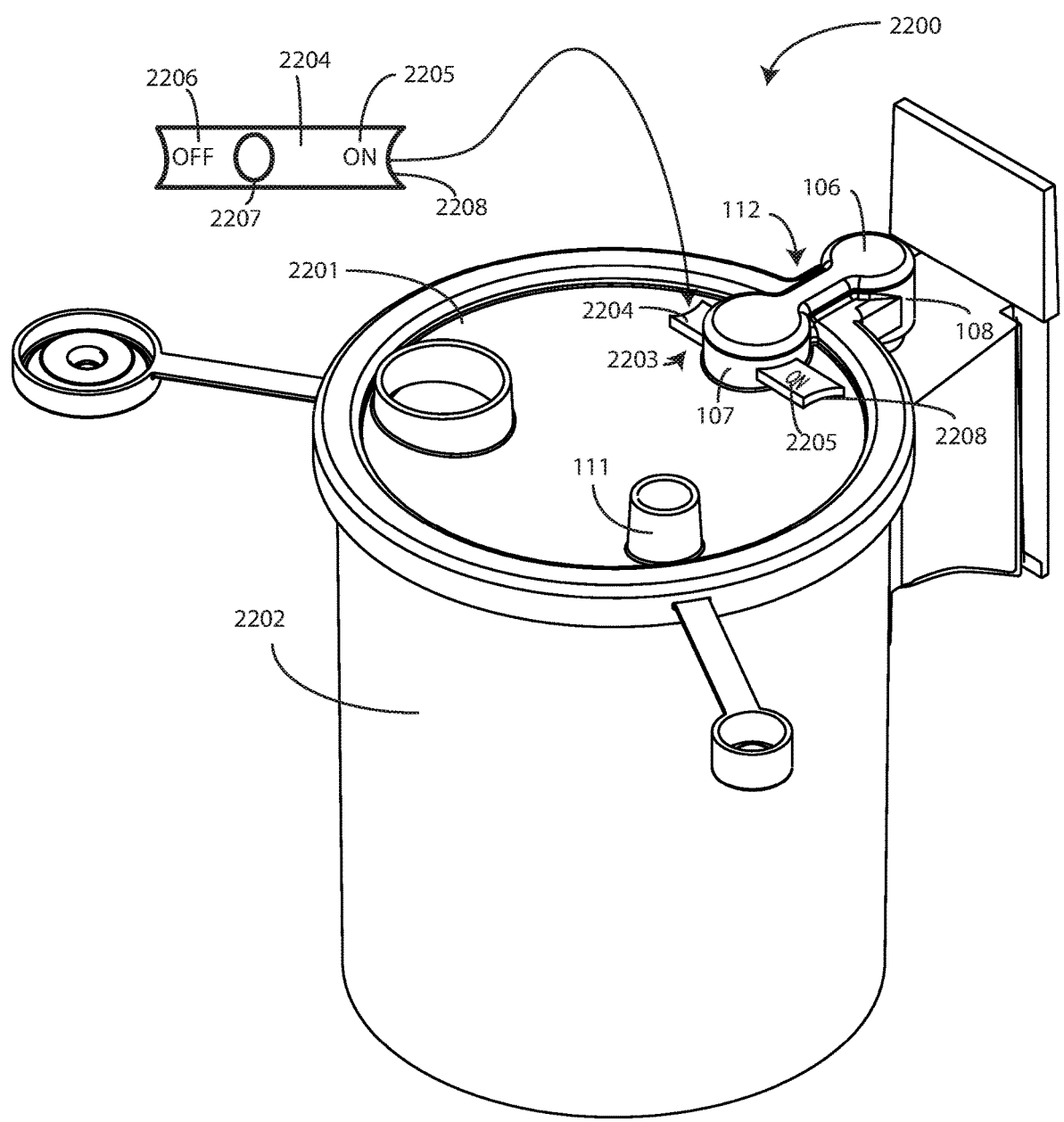
FIG. 22 illustrates a perspective view of another explanatory canister system in accordance with embodiments of the disclosure.

Turning now to FIG. 22, illustrated therein is another explanatory canister system 2200 suitable for use with the hub mount stand (1800) of FIG. 18. As with previous embodiments, the canister system 2200 includes a canister lid 2201 and a canister 2202. A disposable liner (not shown) can be attached to the canister lid 2201 to catch fluids or other materials drawn in through the suction port 111.

As before, a suction conduit 112 comprises a separate suction conduit cap 106 that adhesively sealed to each of a first lobe annular wall 107, the second lobe annular wall 108, and the one or more suction duct sidewalls in one embodiment. The suction conduit 112 comprises a suction duct defined by the suction duct sidewalls, a first lobe annular wall 107, and the second lobe annular wall 108. The suction conduit 112 again resembles a dog bone or double-ended lollipop. The suction conduit 112 is hollow on the inside such that air or other fluid can be drawn through the suction conduit 112. The inclusion of the suction conduit 112 advantageously allows for the elimination of a hose or tube that would traditionally be used to remove air from, or deliver air to, a suction canister.

In this embodiment, the first lobe annular wall 107 comprises a valve 2203 comprising a plank 2204, similar to that described above with reference to FIG. 5. The plank 2204 can be accessed from atop the canister lid 2201 but beneath the suction conduit cap 106. In one embodiment, the plank 2204 includes visual indicia 2205,2206, which in this embodiment is configured as the words "ON" and "OFF."

In the illustrative embodiment of FIG. 22, the plank 2204 includes an aperture 2207 that aligns with the conduit defined axially in the first lobe annular wall 107 when the plank 2204 is in a first position. However, when the plank 2204 is translated laterally to a second position, the aperture 2207 becomes misaligned with the conduit of the first lobe annular wall 107 to prevent the flow of air.

Accordingly, when the plank 2204 is shown in the position of FIG. 22, with the visual indicia 2205 extending from the right side of the conduit defined by the first lobe annular wall 107, the valve 2203 is ON. However, by pushing the concave recess 2208 toward the first lobe annular wall 107, the plank 2204 translates to the left (as shown in FIG. 22) to misalign the aperture 2207 with the conduit defined by the first lobe annular wall 107. The other side of the plank 2204 would then translate out of the first lobe annular wall 107 to present visual indicia 2205 indicating that the valve 2203 is OFF.

Figure 23:
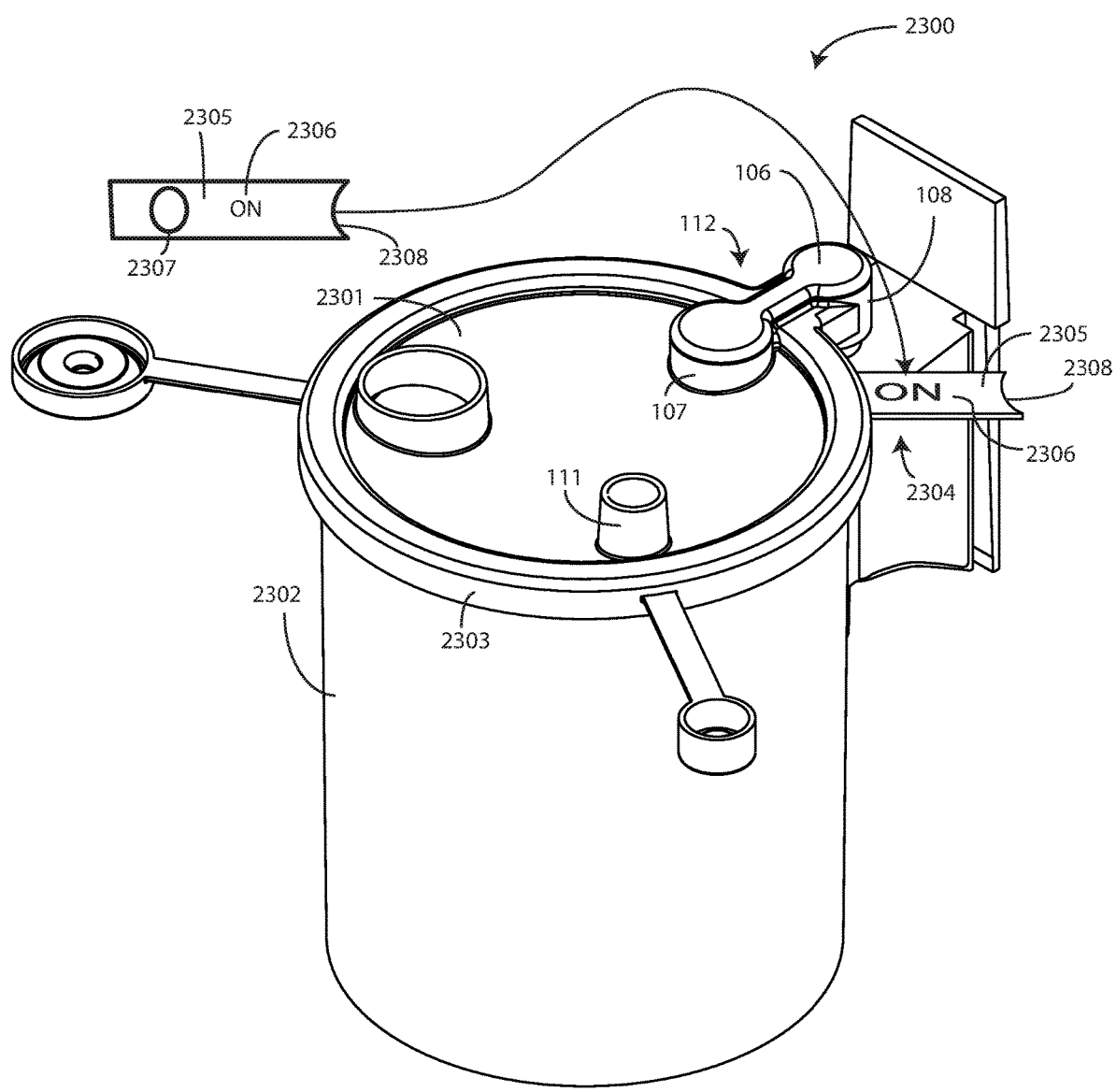
FIG. 23 illustrates a perspective view of another explanatory canister system in accordance with embodiments of the disclosure.

Turning now to FIG. 23, illustrated therein is another explanatory canister system 2300 suitable for use with the hub mount stand (1800) of FIG. 18. As with previous embodiments, the canister system 2300 includes a canister lid 2301 and a canister 2302. A disposable liner (not shown) can be attached to the canister lid 2301 to catch fluids or other materials drawn in through the suction port 111.

As before, a suction conduit 112 comprises a separate suction conduit cap 106 that adhesively sealed to each of a first lobe annular wall 107, the second lobe annular wall 108, and the one or more suction duct sidewalls in one embodiment. The suction conduit 112 comprises a suction duct defined by the suction duct sidewalls, a first lobe annular wall 107, and the second lobe annular wall 108. The suction conduit 112 again resembles a dog bone or double-ended lollipop. The suction conduit 112 is hollow on the inside such that air or other fluid can be drawn through the suction conduit 112. The inclusion of the suction conduit 112 advantageously allows for the elimination of a hose or tube that would traditionally be used to remove air from, or deliver air to, a suction canister.

In this embodiment, the annular perimeter 2303 of the canister lid 2201 includes a valve 2304. The valve 2304 comprises a plank 2305 that can be accessed from the side of the annular perimeter 2303. In one embodiment, the plank 2305 includes visual indicia 2306, which in this embodiment is configured as the word "ON."

In the illustrative embodiment of FIG. 23, the plank 2305 includes an aperture 2307 that aligns with the conduit defined axially in the first lobe annular wall 107 when the plank 2305 is in a first position. However, when the plank 2305 is translated laterally to a second position, the aperture 2307 becomes misaligned with the conduit of the first lobe annular wall 107 to prevent the flow of air.

Accordingly, when the plank 2305 is shown in the position of FIG. 23, with the plank 2305 pulled outwardly from the annular perimeter 2303 of the canister lid 2201, this allows visual indicia 2306 to become visible, thereby indicating that the valve 2304 is ON. However, by pushing the concave recess 2308 toward the annular perimeter 2303, the plank 2305 translates to the left (as shown in FIG. 23) to misalign the aperture 2307 with the conduit defined by the first lobe annular wall 107. This causes the visual indicia 2306 to translate into the lid 2301, where it cannot be seen. The absence of the visual indicia 2306 indicates that the valve 2304 is OFF.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims. Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. A canister system, comprising:
a canister comprising a cylindrical sidewall, a mechanical support extending orthogonally from the cylindrical sidewall, a mounting bracket coupled to the mechanical support, and a tubeless vacuum connection port extending laterally through the mechanical support to the mounting bracket; and
a hub mount vacuum source comprising at least one canister receiver to receive the mounting bracket, the canister receiver comprising a vacuum port that aligns with the tubeless vacuum connection port when the mounting bracket seats within the at least one canister receiver, the hub mount vacuum source comprising one or more internal manifolds connecting the vacuum port to a central vacuum source connection.

2. The canister system of claim 1, the hub mount vacuum source comprising a first hub mount vacuum source portion separable from a second hub mount source portion to expose the one or more internal manifolds.

3. The canister system of claim 2, further comprising at least one actuation switch allowing the vacuum port to be selectively turned ON or OFF.

4. The canister system of claim 1, further comprising a canister lid coupled to the canister, the canister lid comprising an annular perimeter interrupted by a suction conduit defined by a suction duct separating a first lobe and a second lobe, the first lobe disposed interior of the annular perimeter, the second lobe disposed exterior to the annular perimeter, and the suction duct traversing the annular perimeter.

5. The canister system of claim 4, the canister comprising a valve coupled to the mechanical support, the valve defining a duct from the second lobe of the canister lid when the canister lid is coupled to the canister.

6. The canister system of claim 5, the valve disposed between the second lobe and the mechanical support.

7. The canister system of claim 6, the valve further comprising a shaft terminating at a push button, the shaft selectively translatable laterally between a first position and a second position to turn the valve ON or OFF, respectively.

8. The canister system of claim 7, the shaft comprising visual indicia to indicate whether the valve is ON or OFF.

9. The canister system of claim 8, the visual indicia comprising a recess defined in the shaft.

10. The canister system of claim 6, the valve comprising a plank selectively translatable laterally between a first position and a second position to turn the valve ON or OFF, respectively.

11. The canister system of claim 10, the plank defining a concave recess at an end of the plank.

12. The canister system of claim 10, the plank comprising visual indicia to indicate whether the valve is ON or OFF.

13. The canister system of claim 10, the visual indicia comprising one or more of color coding or text.

14. The canister system of claim 6, the valve comprising a twisting control mechanism to selectively rotate about the valve between a first position and a second position to turn the valve ON or OFF.

15. The canister system of claim 14, the twisting control mechanism comprising a paddle responsive to a force to axially rotate the twisting control mechanism about the valve.

16. The canister system of claim 6, wherein the valve is selectively detachable from the mechanical support.

17. The canister system of claim 16, wherein the mechanical support is disposed between the valve and the second lobe, wherein the valve comprises:

a plank disposed between two O-ring seals, the plank defining an aperture to selectively align with a conduit defined axially in the valve to turn the valve ON; and a rubber valve insert that allows the valve to be removably inserted into a valve receiver of the canister disposed beneath the mechanical support.

18. A canister system, comprising:

a canister comprising a cylindrical sidewall, a mechanical support extending orthogonally from the cylindrical sidewall, a mounting bracket coupled to the mechanical support, and a tubeless vacuum connection port extending laterally through the mechanical support to the mounting bracket;

a hub mount vacuum source comprising at least one canister receiver to receive the mounting bracket, the canister receiver comprising a vacuum port that aligns with the tubeless vacuum connection port when the mounting bracket seats within the at least one canister receiver, the hub mount vacuum source comprising one or more internal manifolds connecting the vacuum port to a central vacuum source connection a canister lid, selectively attachable to the canister, the canister lid comprising an annular perimeter interrupted by a suction conduit defined by a suction duct separating a first lobe and a second lobe, the first lobe disposed interior of the annular perimeter, the second lobe disposed exterior to the annular perimeter, and the suction duct traversing the annular perimeter;

a valve that is selectively detachable from the mechanical support; and a hub mount stand comprising at least one mounting bracket to receive the mounting bracket.

19. The canister system of claim 18, the hub mount stand comprising one or more flat surfaces supporting the at least one mounting bracket, a central column coupled to the one or more flat surfaces, and a base comprising one or more casters, the base supporting the central column.

* * * * *